(12) United States Patent
Cho et al.

(10) Patent No.: US 12,186,365 B2
(45) Date of Patent: Jan. 7, 2025

(54) COMPOSITION FOR REGULATING CELL DIVISION COMPRISING FCHO1 MODULATOR, AND METHOD FOR REGULATING CELL DIVISION USING SAME

(71) Applicant: SEOUL NATIONAL UNIVERSITY R&DB FOUNDATION, Seoul (KR)

(72) Inventors: Myung Haing Cho, Seoul (KR); Sung Jin Park, Jangan-gu Gyeonggi-do (KR); Jong Sun Park, Daejeon (KR); Kwang Pyo Kim, Seoul (KR)

(73) Assignees: Seoul National University R&DB Foundation, Seoul (KR); The IAC in Chungnam National University, Daejeon (KR); UIC Group of Kyung Hee University, Gyeonggi-do (KR)

( * ) Notice: Subject to any disclaimer, the term of this patent is extended or adjusted under 35 U.S.C. 154(b) by 1 day.

(21) Appl. No.: 15/776,897

(22) PCT Filed: Nov. 17, 2016

(86) PCT No.: PCT/KR2016/013304
§ 371 (c)(1),
(2) Date: May 17, 2018

(87) PCT Pub. No.: WO2017/086725
PCT Pub. Date: May 26, 2017

(65) Prior Publication Data
US 2019/0085093 A1    Mar. 21, 2019

(30) Foreign Application Priority Data

Nov. 17, 2015  (KR) .................... 10-2015-0161326
Nov. 17, 2016  (KR) .................... 10-2016-0153654

(51) Int. Cl.
| | |
|---|---|
| *A61K 38/17* | (2006.01) |
| *A61K 31/713* | (2006.01) |
| *A61P 35/00* | (2006.01) |
| *C07K 14/47* | (2006.01) |
| *C07K 16/28* | (2006.01) |
| *C07K 16/30* | (2006.01) |
| *C12N 15/113* | (2010.01) |
| *G01N 33/574* | (2006.01) |

(52) U.S. Cl.
CPC ........ *A61K 38/1709* (2013.01); *A61K 31/713* (2013.01); *A61P 35/00* (2018.01); *C07K 16/28* (2013.01); *C07K 16/3023* (2013.01); *C07K 16/3076* (2013.01); *C12N 15/113* (2013.01); *G01N 33/57484* (2013.01); *G01N 33/57492* (2013.01); *C12N 2310/14* (2013.01)

(58) Field of Classification Search
CPC .............................................. A61K 38/1709
See application file for complete search history.

(56) References Cited

U.S. PATENT DOCUMENTS

| | | | | |
|---|---|---|---|---|
| 8,003,595 | B2 * | 8/2011 | Avrameas | A61K 47/6811 514/1.1 |
| 8,163,896 | B1 * | 4/2012 | Bentwich | C07K 14/4702 536/24.5 |
| 2003/0118610 | A1 * | 6/2003 | Stern | A61P 5/18 424/208.1 |
| 2004/0137572 | A1 * | 7/2004 | Finney | C12N 15/85 435/69.1 |
| 2008/0020990 | A1 * | 1/2008 | Yano | A61P 43/00 514/44 A |
| 2008/0057066 | A1 * | 3/2008 | Dixit | A61P 35/00 424/139.1 |
| 2009/0169485 | A1 * | 7/2009 | Cho | A61P 35/00 514/1.1 |
| 2011/0008422 | A1 * | 1/2011 | Dekel | A61K 47/6911 424/450 |
| 2013/0108548 | A1 * | 5/2013 | Vlieghe | A61K 47/64 424/1.69 |
| 2014/0364328 | A1 * | 12/2014 | Nagele | G01N 33/6893 506/9 |

FOREIGN PATENT DOCUMENTS

| | | |
|---|---|---|
| KR | 10-2010-0093301 | 8/2010 |
| WO | 2012/009567 | 1/2012 |

OTHER PUBLICATIONS

Ju (Proceedings of the National Academy of Sciences, U.S.A., vol. 88, p. 2658-2662, 1991) (Year: 1991).*
Martindale (Nature Genetics, vol. 18, p. 150-154, 1998) (Year: 1998).*
Nonaka (Human Molecular Genetics, vol. 18, No. 18, p. 3353-3364, 2009) (Year: 2009).*
Mendoza (Arch. Immunol. Ther. Exp., vol. 53, p. 47-60, 2005) (Year: 2005).*
Gao et al (The AAPS Journal, 2007, 9:E92-E104) (Year: 2007).*
Parker et al (Expert Reviews in Molecular Medicine, 2003, 5:1-15) (Year: 2003).*
Verma and Somia (Nature, 1997, 389:239-242) (Year: 1997).*
McNaughton (Proceedings of the National Academy of Sciences, USA, vol. 106, No. 15, p. 6111-6116, 2009) (Year: 2009).*
Eck and Wilson (Goodman & Gilman's The Pharmacological basis of Therapeutics, 1996, McGraw-Hill, New York, NY. p. 77-101) (Year: 1996).*
Niidome and Huang (Gene Therapy, 2002, 9:1647-1652) (Year: 2002).*

(Continued)

*Primary Examiner* — Michael Allen
(74) *Attorney, Agent, or Firm* — Ping Wang; Kalos Athena Wang PLLC

(57) ABSTRACT

The present invention relates to a composition for regulating cell division by promoting or inhibiting the activity of FCHo1, and a method for regulating cell division using the same. The FCHo1 activity regulator of the present invention targets FCHo1 which functions as an important factor in cell division, and promotes or inhibits the activity thereof, thereby promoting cell division or inhibiting cell division, and thus can be effectively utilized for the treatment of diseases associated with cell division.

3 Claims, 14 Drawing Sheets

Specification includes a Sequence Listing.

(56) References Cited

OTHER PUBLICATIONS

Zhang et al (Molecular Therapy, 2012, 20:1298-1304) (Year: 2012).*
Burgess et al. (J of Cell Bio. 111:2129-2138, 1990) (Year: 1990).*
Lazar et al. (Molecular and Cellular Biology 8:1247-1252, 1988) (Year: 1988).*
Baker (Immunity, vol. 13, p. 475-484, 2000) (Year: 2000).*
Komenaka et al., Clinics in Dermatology, 2004, vol. 22, p. 251-265 (Year: 2004).*
Evans et al. (Q. J. Med 1999: 92: 299-307) (Year: 1999).*
Schiffman et al., The New England Journal of Medicine, vol. 353, No. 20, p. 2101-2104, 2005 (Year: 2005).*
Cuzick et al. (The Lancet, vol. 361, p. 296-300, 2003) (Year: 2003).*
Hernandez-Ledesma (Peptides, vol. 30, p. 426-430, 2009) (Year: 2009).*
Skop, A. R. et al., "Dissection of the Mammalian Midbody Proteome Reveals Conserved Cytokinesis Mechanisms", Science, 2004, vol. 305(5680), pp. 61-66.
Dambournet, D. et al., "Rab35 GTPase and OCRL phosphatase remodel lipids and F-actin for successful cytokinesis", Nature Cell Biology, 2011, vol. 13, pp. 981-988. (Abstract only).
Guizetti, J. et al., "Cortical Constriction During Abscission Involves Helices of ESCRT-III-Dependent Filaments", Science, 2011, vol. 331, pp. 1616-1620.
Lafaurie-Janvore, J. et al., "ESCRT-III assembly and cytokinetic abscission are induced by tension release in the intercellular bridge", Science, 2013, vol. 339(6127), pp. 1625-1629. (Abstract only).
Liu, S. et al., "F-BAR family proteins, emerging regulators for cell membrane dynamic changes-from structure to human diseases", Journal of Hematology & Oncology, 2015, vol. 8(47), pp. 2-14.
Sakaushi, S. et al., "Dynamic Behavior of FCHO1 Revealed by Live-Cell Imaging Microscopy: Its Possible Involvement in Clathrin-Coated Vesicle Formation", Bioscience, Biotechnology, and Biochemistry, 2007, vol. 71(7), pp. 1764-1768.
Umasankar, P. K. et al., "Distinct and separable activities of the endocytic clathrin-coat components Fcho 1/2 and AP-2 in developmental patterning", Nature Cell Biology, 2012, vol. 14, pp. 488-501. (Abstract only).
International Search Report and Written Opinion of International Searching Authority of International Application No. PCT/KR2016/013304 mailed Feb. 22, 2017.

* cited by examiner

【fig. 1】
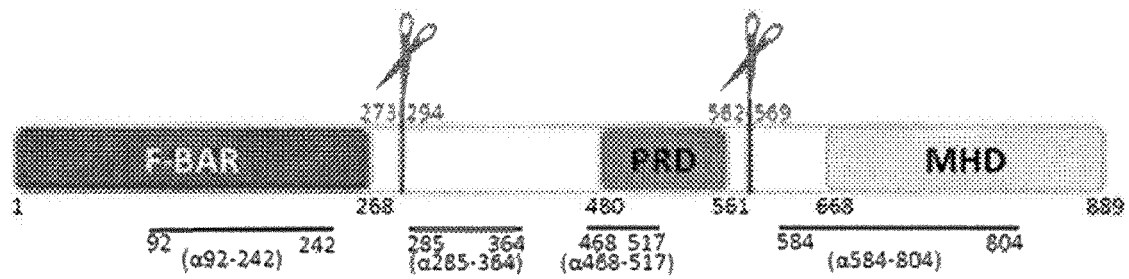
【fig. 2】
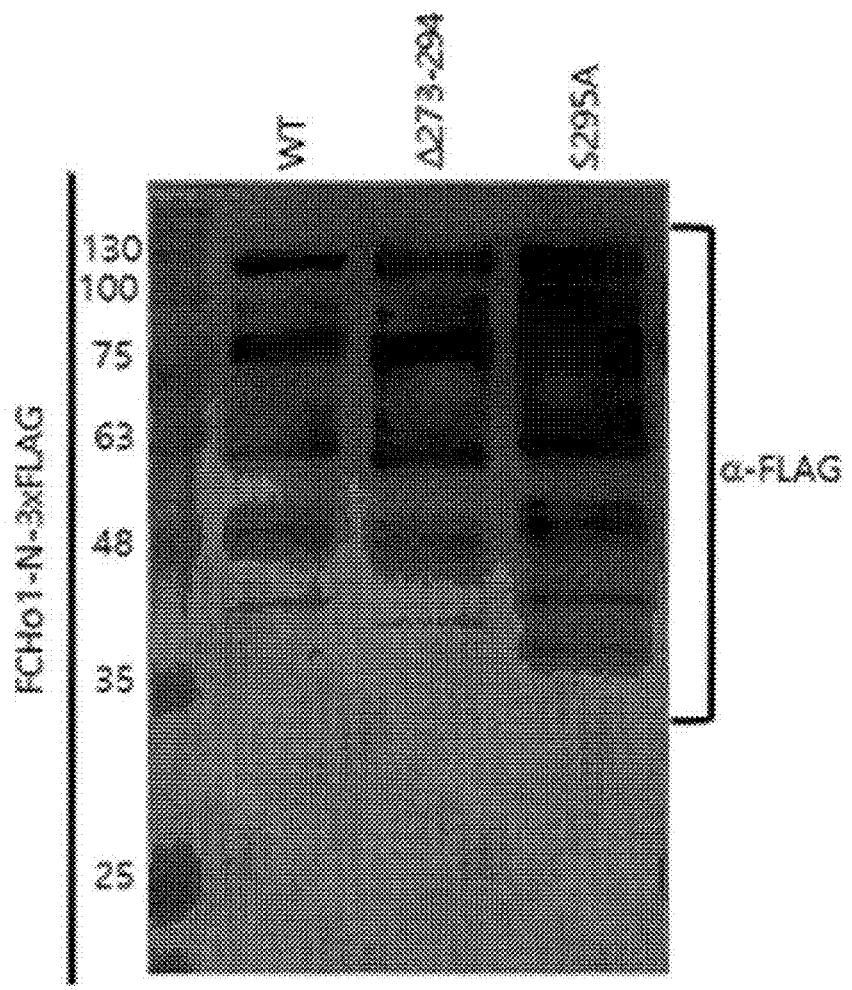

[fig. 3]
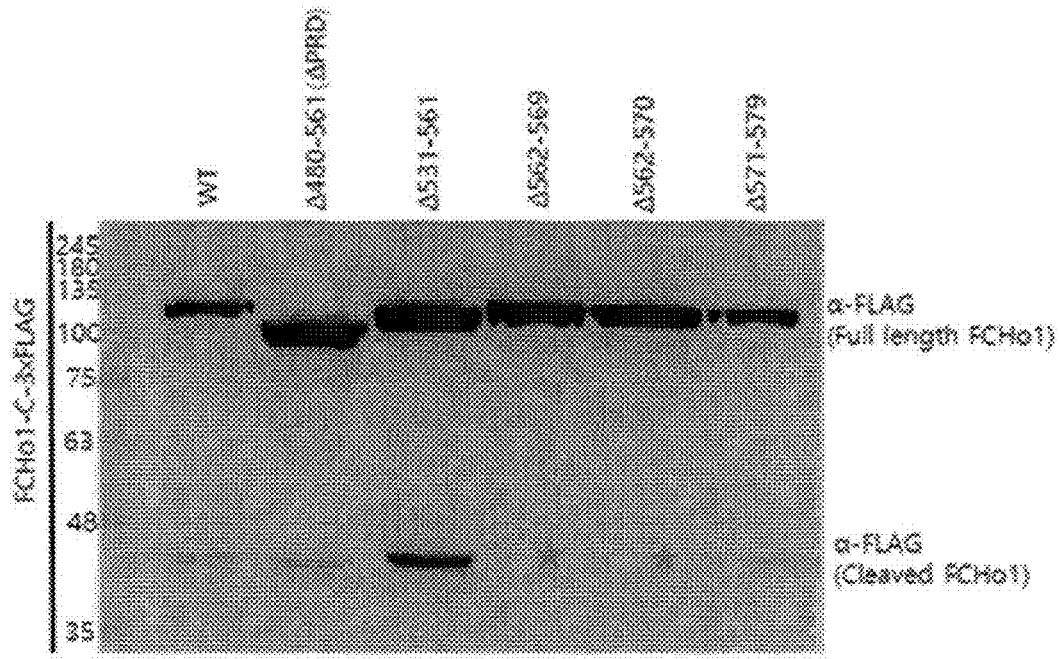
[fig. 4]
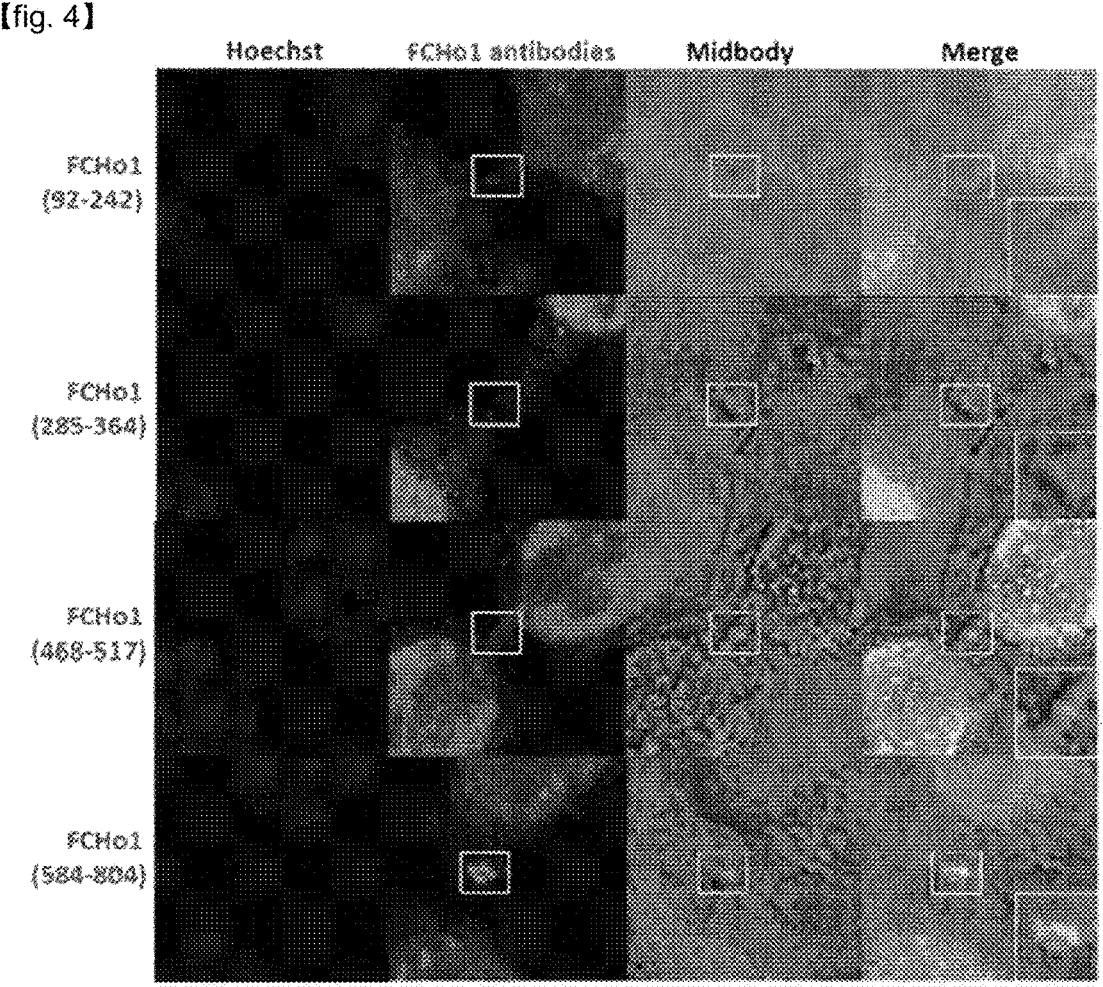

[fig. 5]
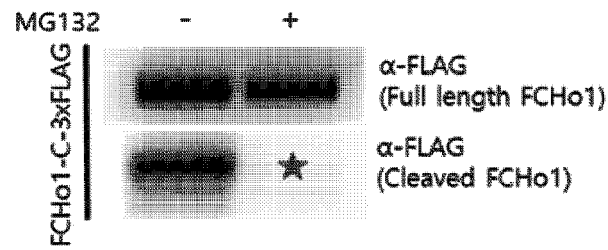
[fig. 6]
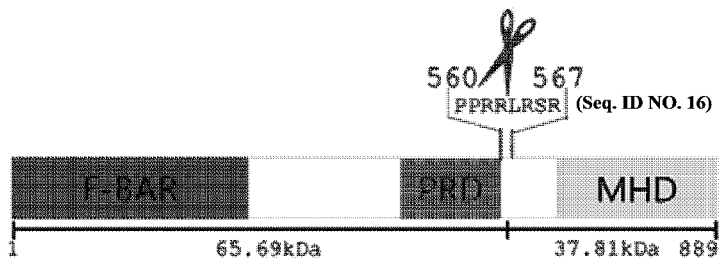
[fig. 7]
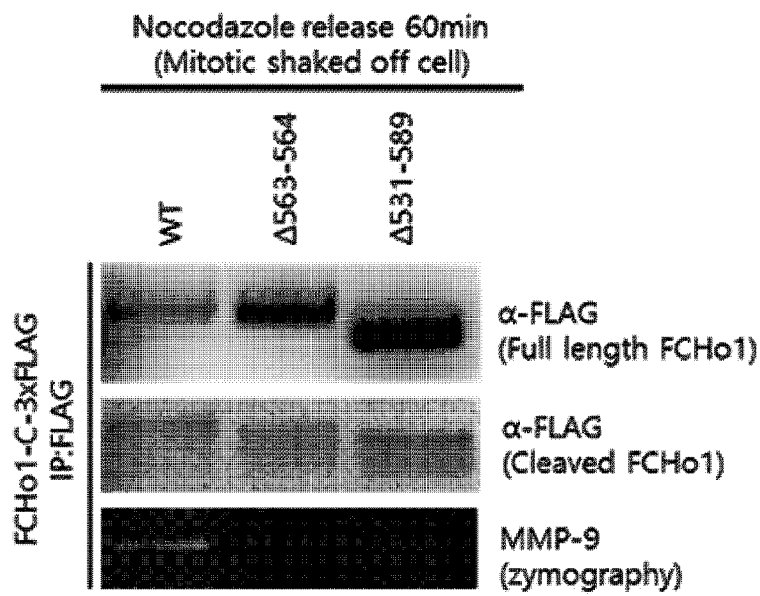

[fig. 8]
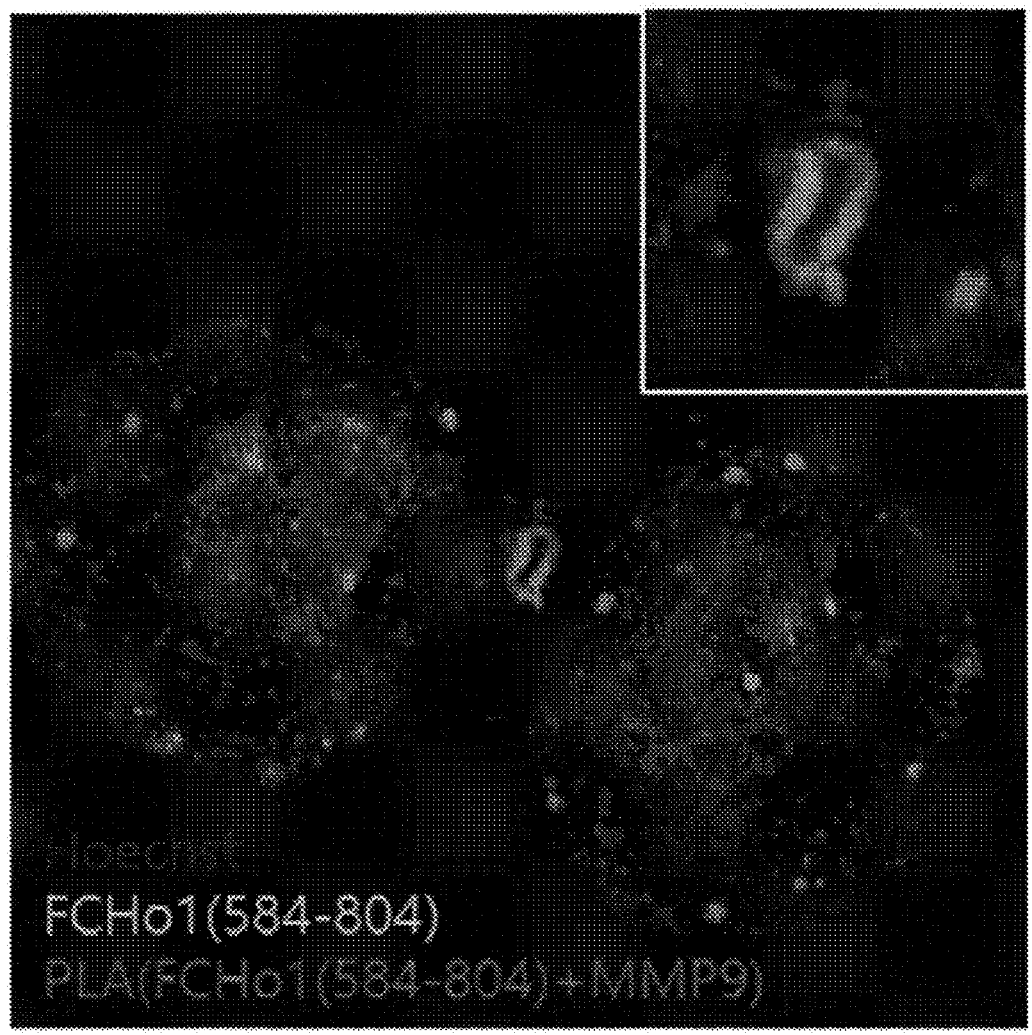

[fig. 9]
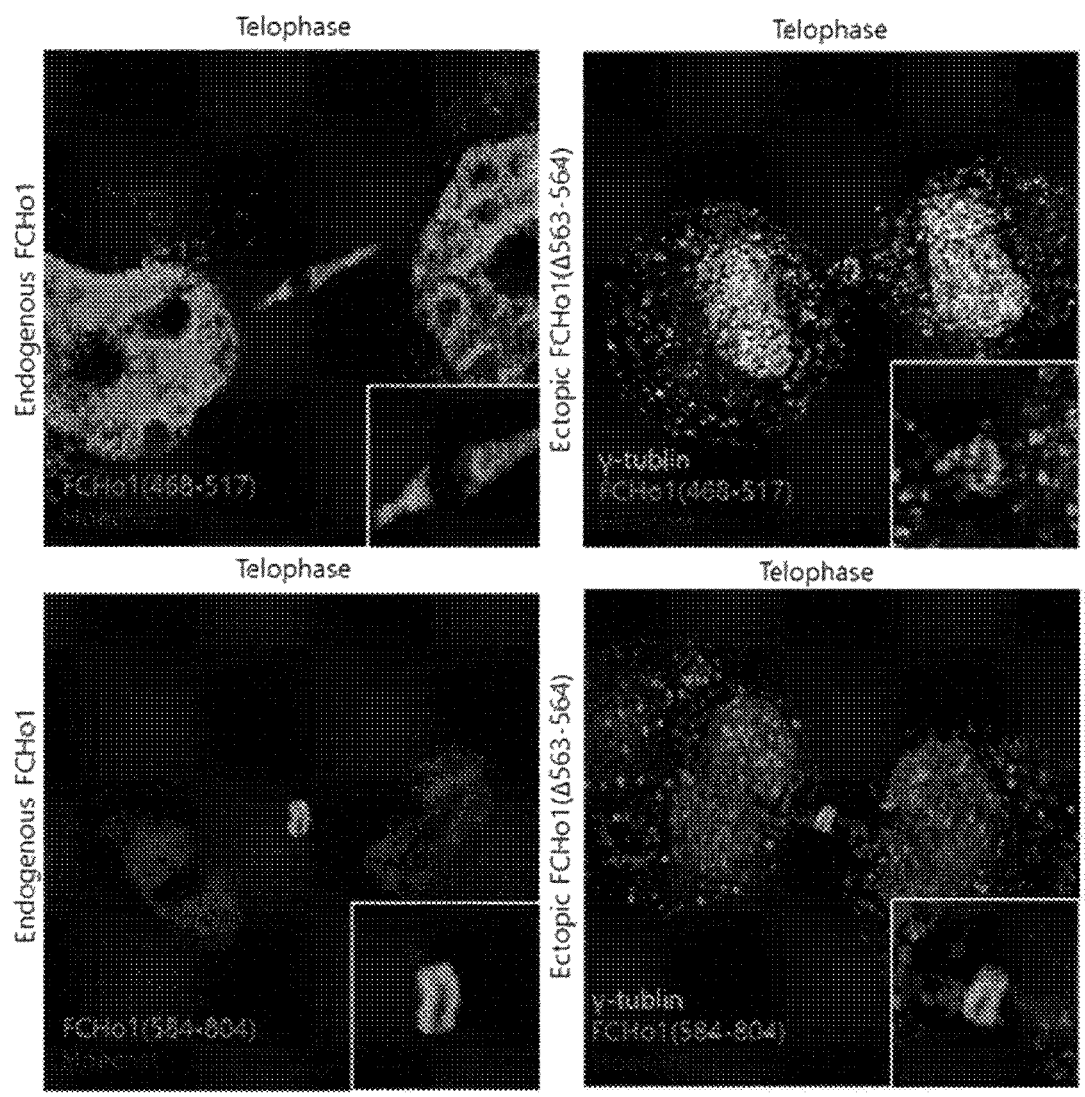

[fig. 10]
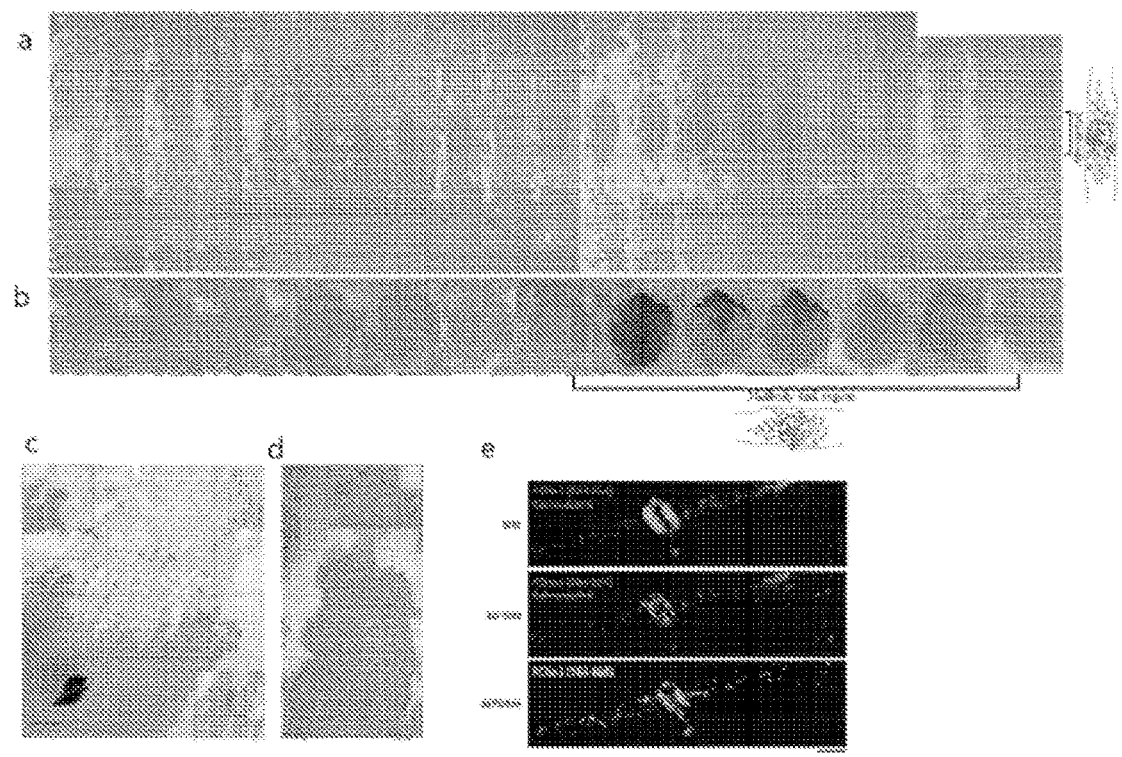
[fig. 11]
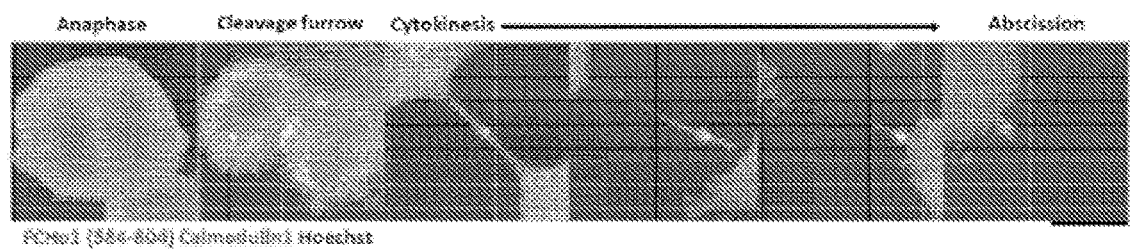
[fig. 12]

[fig. 13]
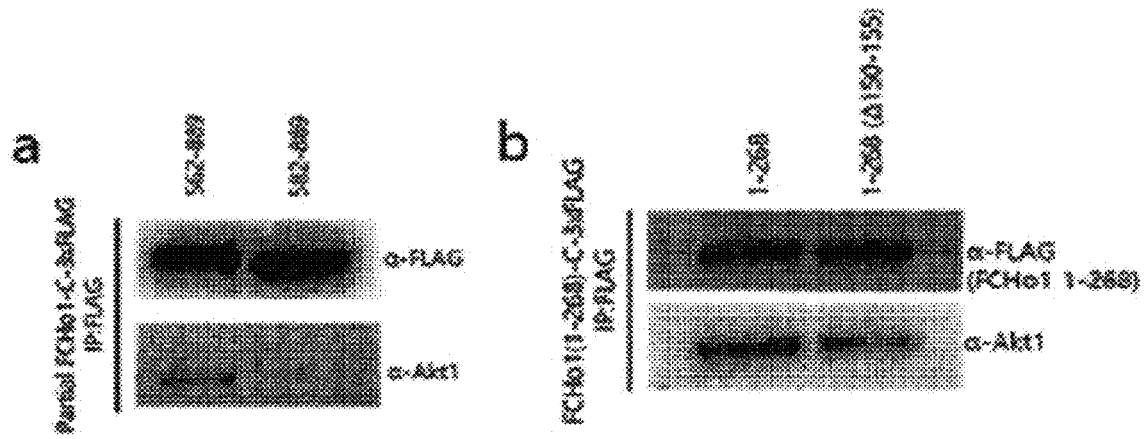
[fig. 14]
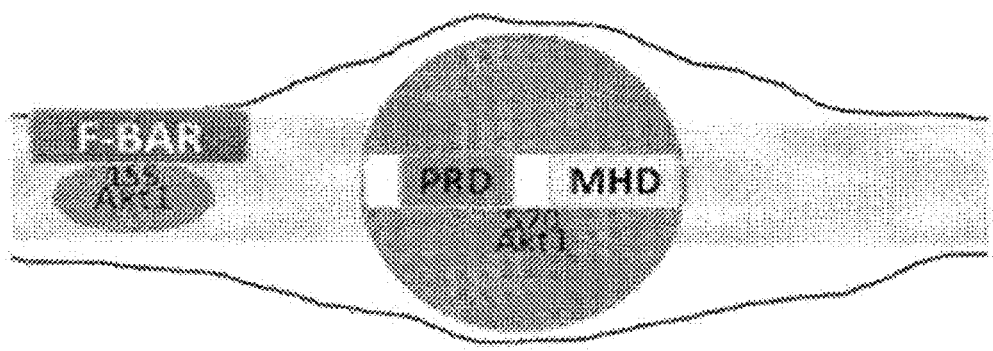
[fig. 15]
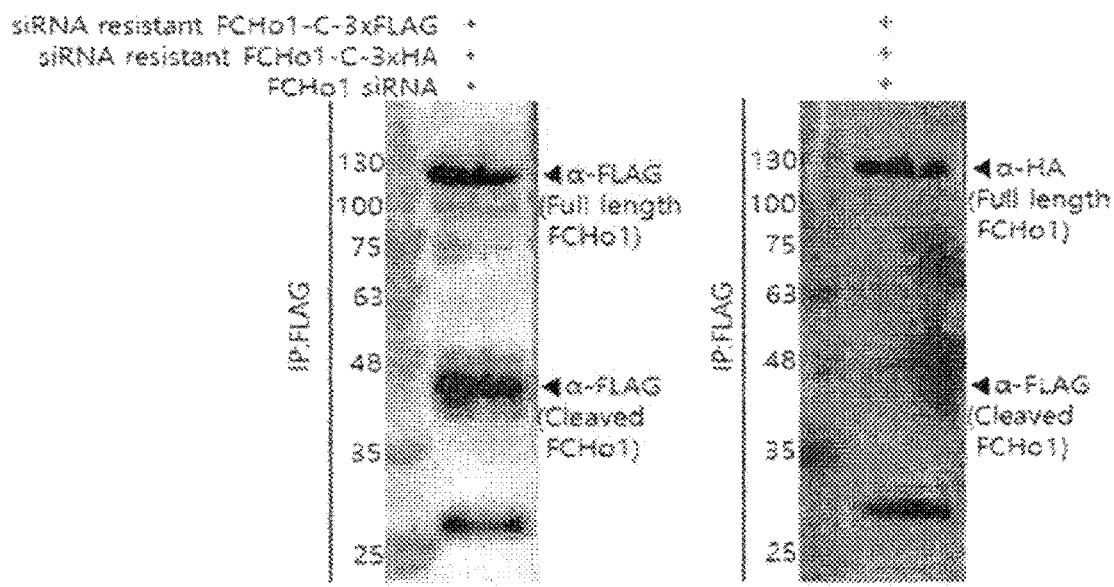

[fig. 16]
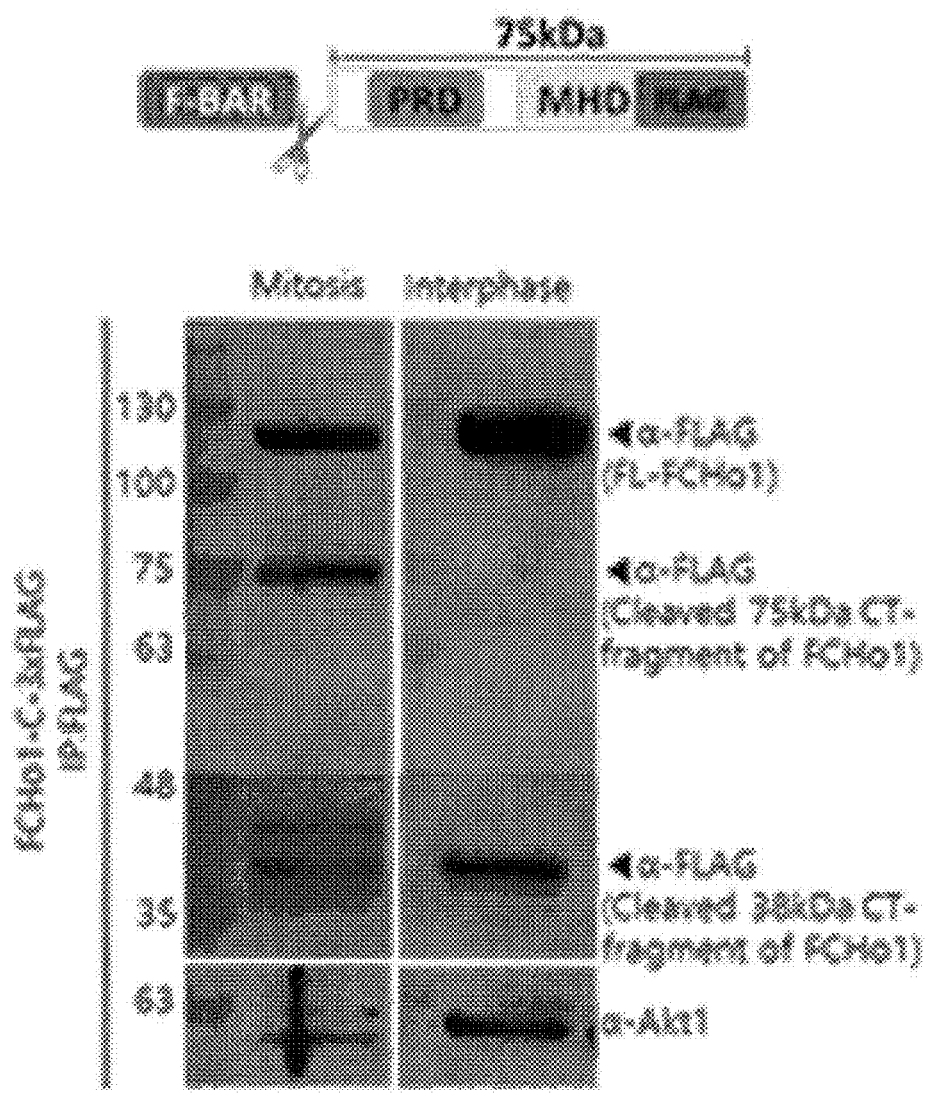

[fig. 17]
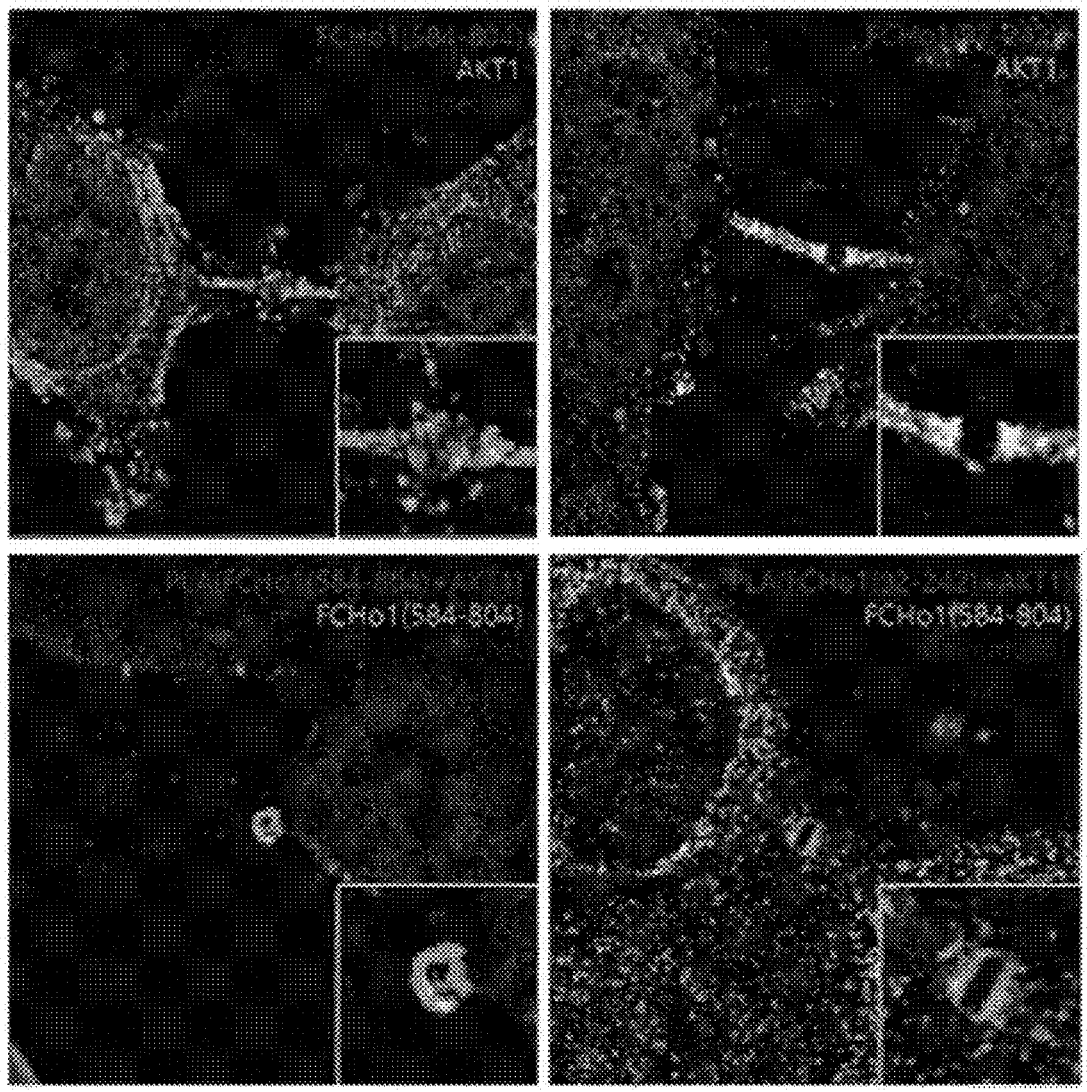
[fig. 18]
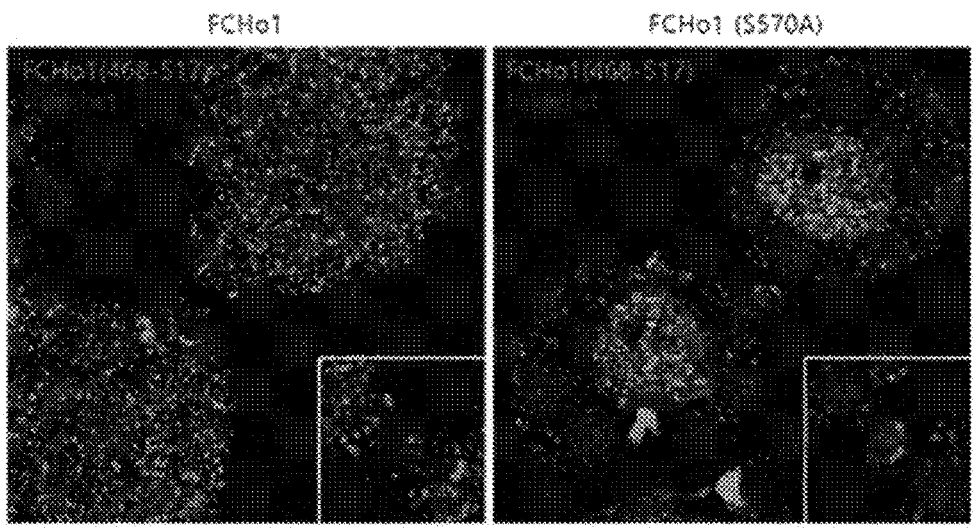

[fig. 19]
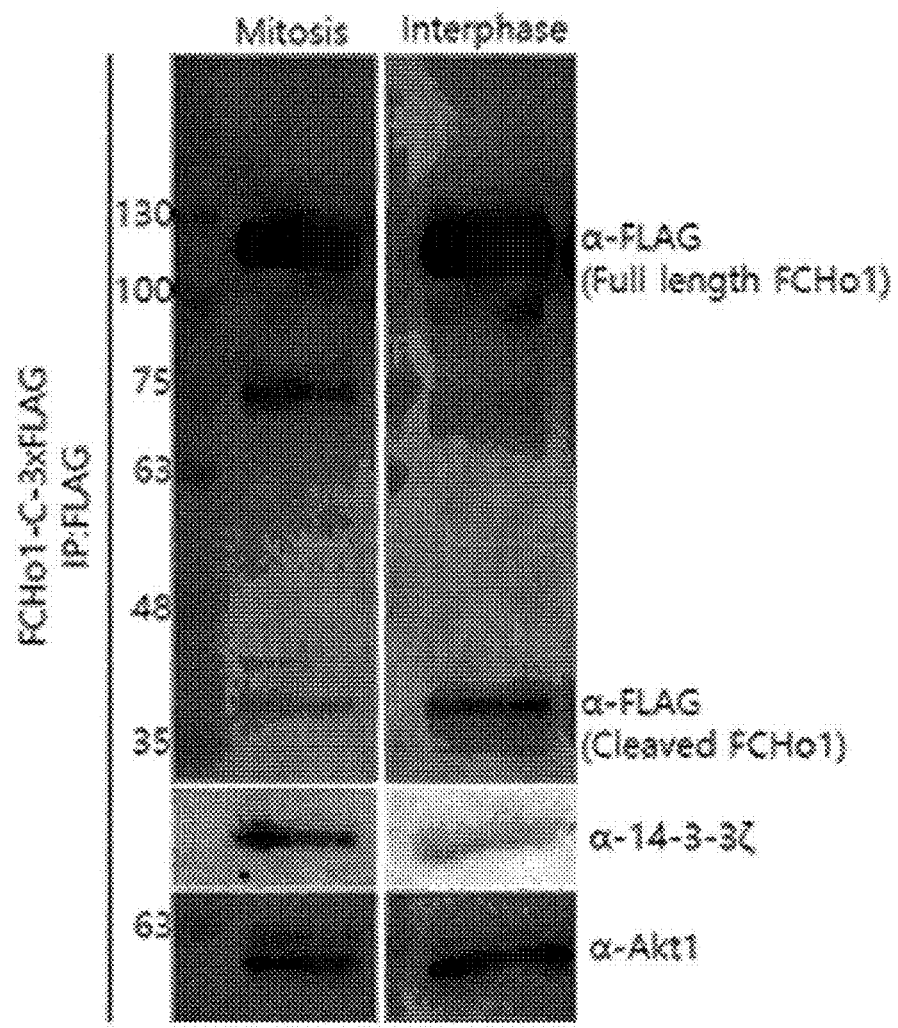
[fig. 20]
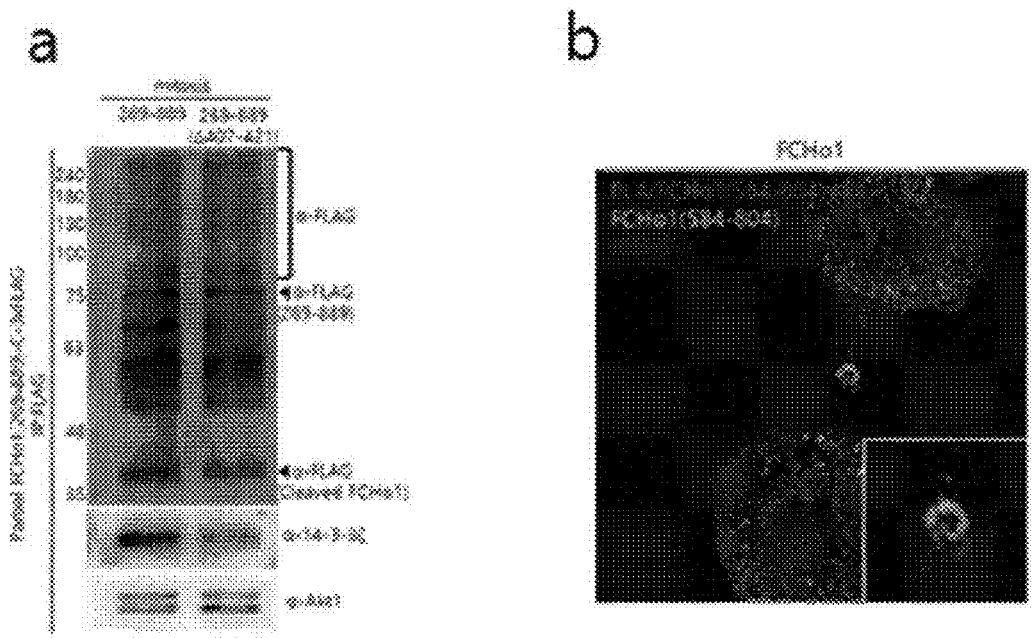

[fig. 21]
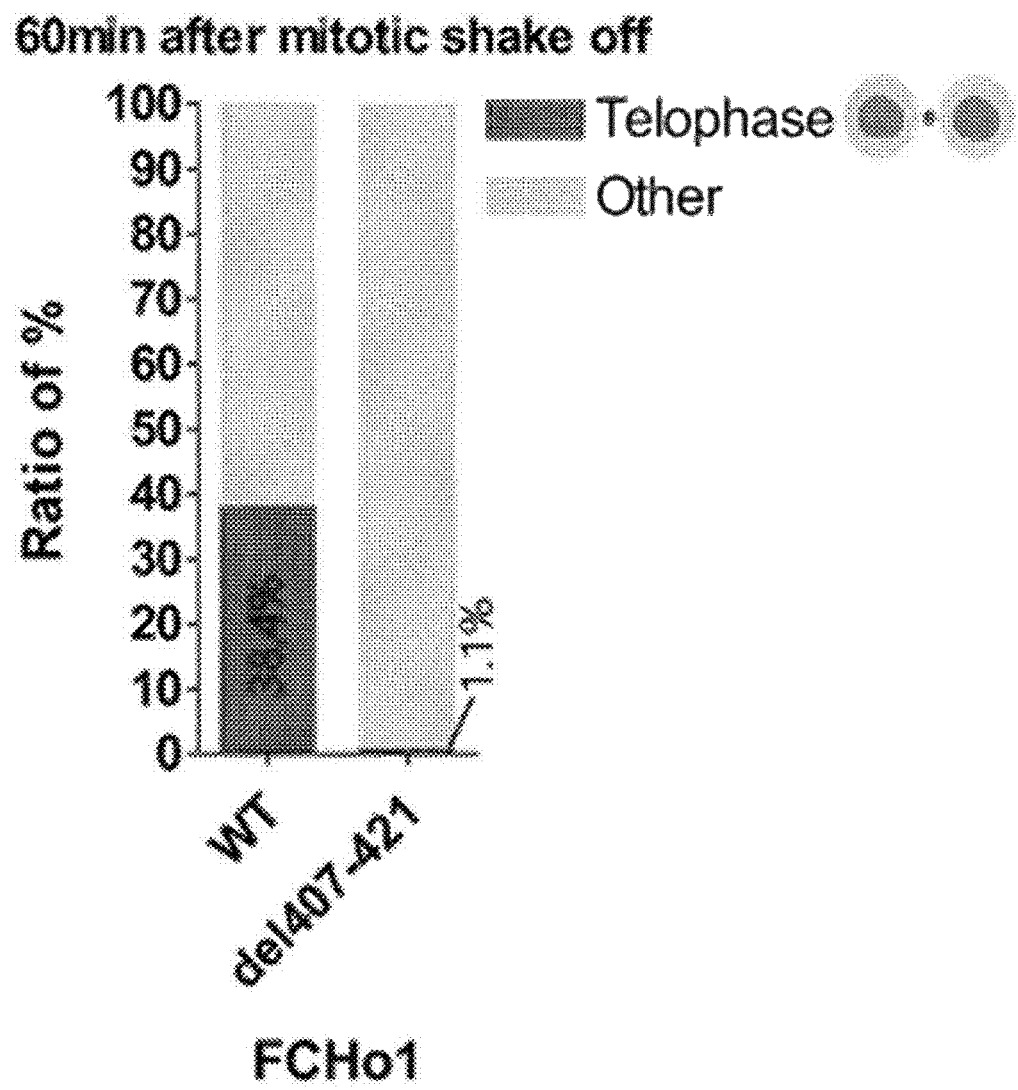

[fig. 22]
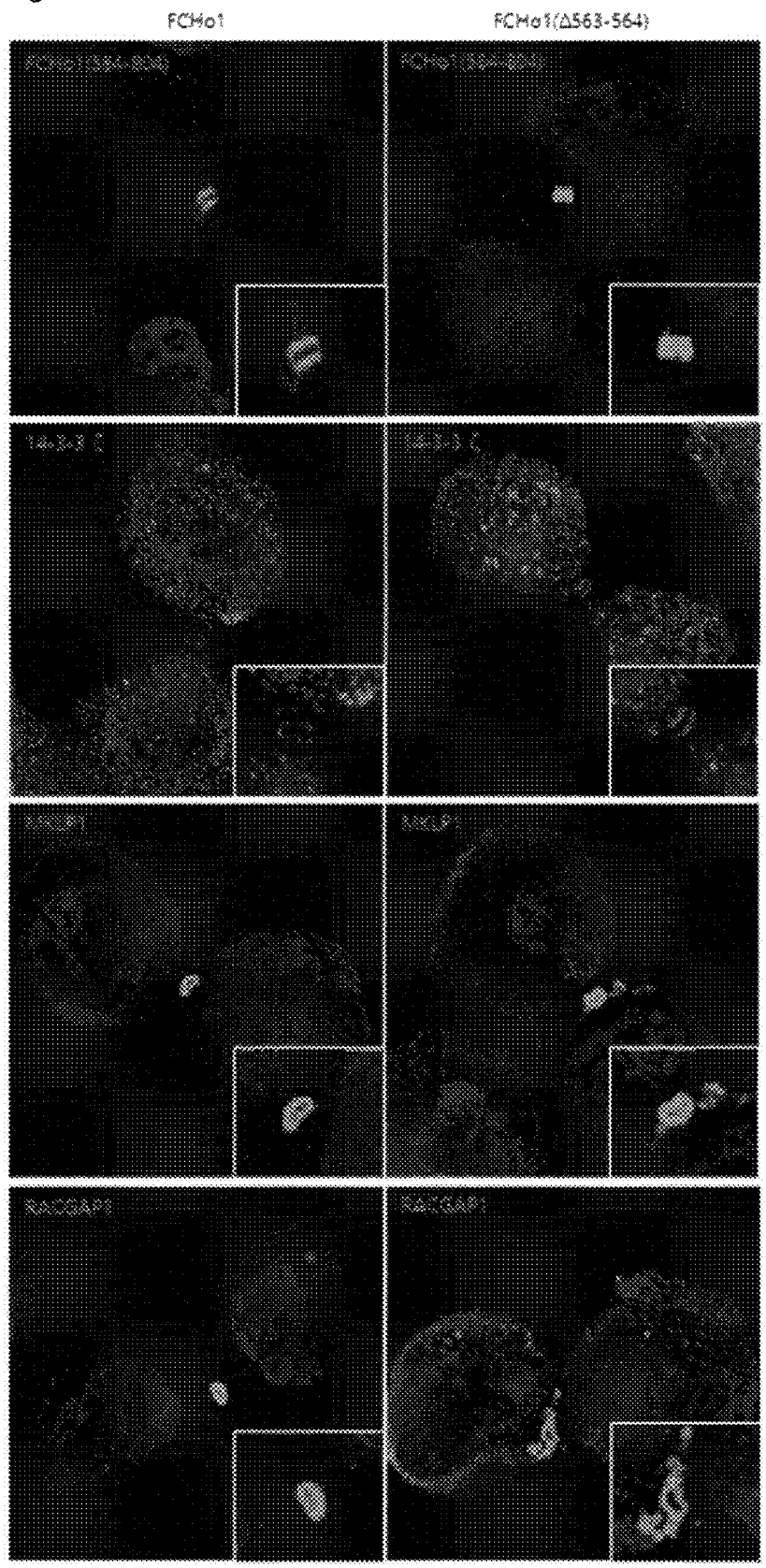

[fig. 23]
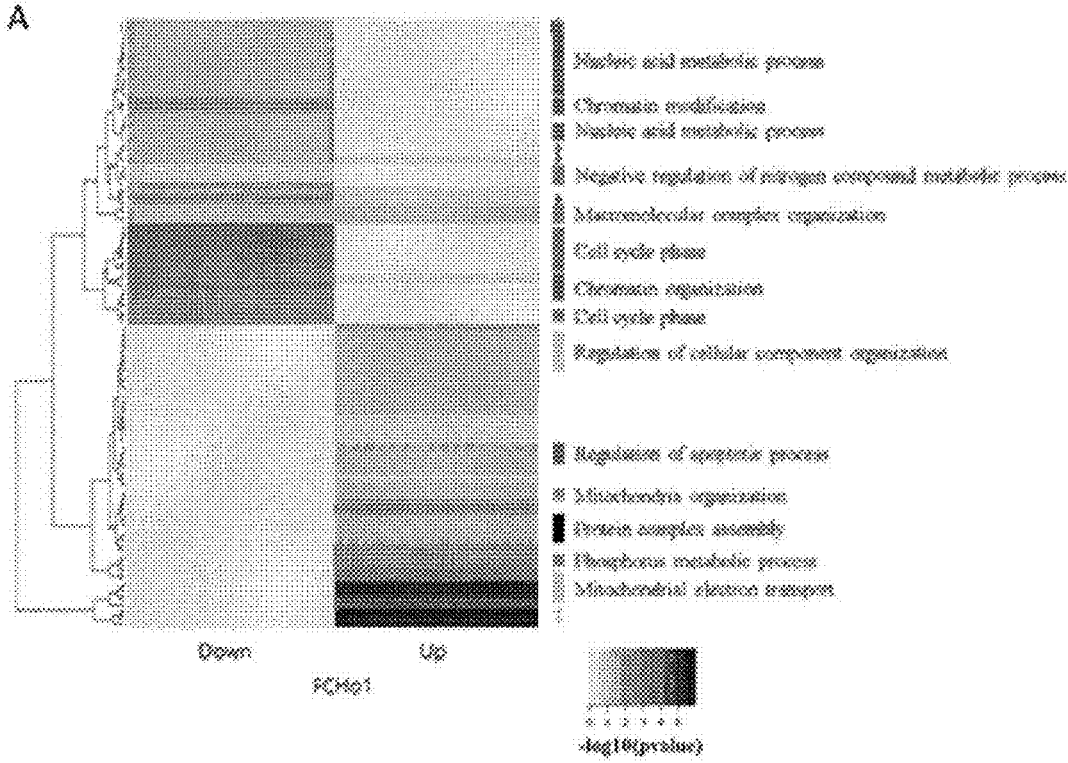
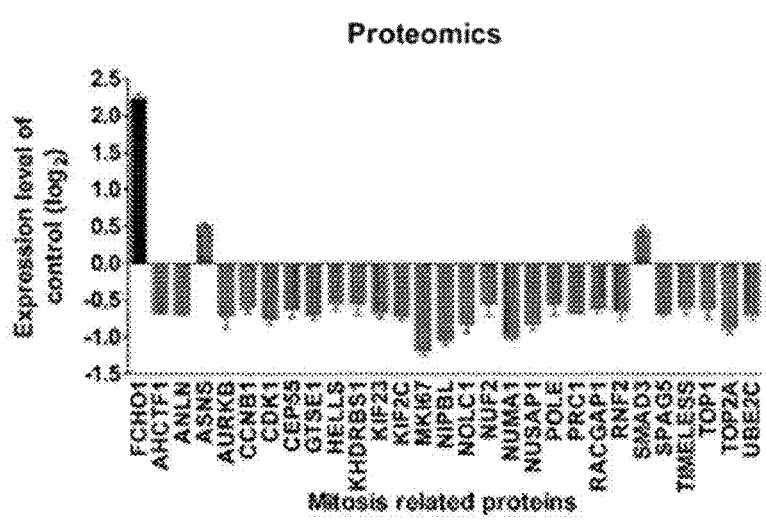

[fig. 24]
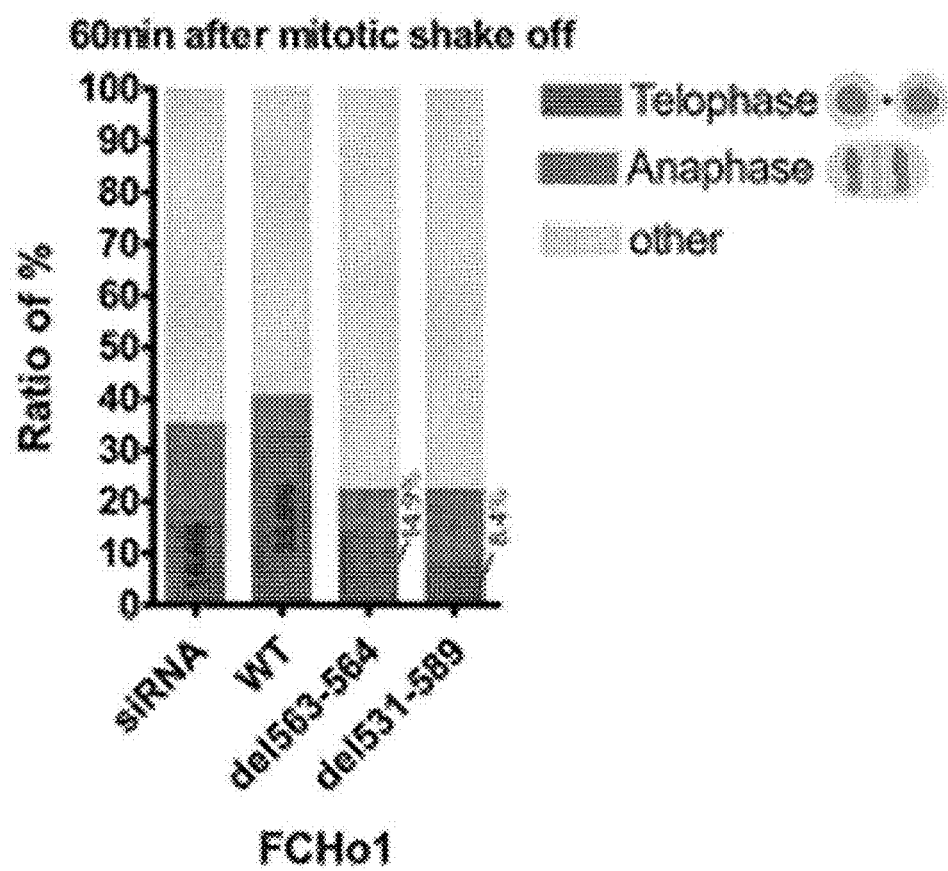

ND METHOD FOR

SEQUENCE LISTING

<160> NUMBER OF SEQ ID NOS: 29

<210> SEQ ID NO 1
<211> LENGTH: 42
<212> TYPE: RNA
<213> ORGANISM: Artificial
<220> FEATURE:
<223> OTHER INFORMATION: shmFCHo1_238

<400> SEQUENCE: 1
aaacuggcac ugugccaccu cucgguggca cagugccagu uu        42

<210> SEQ ID NO 2
<211> LENGTH: 42
<212> TYPE: RNA
<213> ORGANISM: Artificial
<220> FEATURE:
<223> OTHER INFORMATION: shmFCHo1_458

<400> SEQUENCE: 2
gagagaacac cagccagaau cucuucuggc ugguguucuc uc        42

<210> SEQ ID NO 3
<211> LENGTH: 42
<212> TYPE: RNA
<213> ORGANISM: Artificial
<220> FEATURE:
<223> OTHER INFORMATION: shmFCHo1_599

<400> SEQUENCE: 3
uucaggccau ggaggaggcu cucgccuccu ccauggccug aa        42

<210> SEQ ID NO 4
<211> LENGTH: 42
<212> TYPE: RNA
<213> ORGANISM: Artificial
<220> FEATURE:
<223> OTHER INFORMATION: shmFCHo1_1090

<400> SEQUENCE: 4
gccguggccu gcagcucugu cuccagagcu gcaggccacg gc        42

<210> SEQ ID NO 5
<211> LENGTH: 889
<212> TYPE: PRT
<213> ORGANISM: Homo sapiens

<400> SEQUENCE: 5

Met Ser Tyr Phe Gly Glu His Phe Trp Gly Glu Lys Asn His Gly Phe
1               5                   10                  15

Glu Val Leu Tyr His Ser Val Lys Gln Gly Pro Ile Ser Thr Lys Glu
            20                  25                  30

Leu Ala Asp Phe Ile Arg Glu Arg Ala Thr Ile Glu Gly Thr Tyr Ser
        35                  40                  45

Lys Ala Met Ala Lys Leu Ser Lys Leu Ala Ser Asn Gly Thr Pro Met
    50                  55                  60

Gly Thr Phe Ala Pro Leu Trp Glu Val Phe Arg Val Ser Ser Asp Lys
65                  70                  75                  80

Leu Ala Leu Cys His Leu Glu Leu Thr Arg Lys Leu Gln Asp Leu Ile
                85                  90                  95

Lys Asp Val Leu Arg Tyr Gly Glu Glu Gln Leu Lys Thr His Lys Lys
            100                 105                 110

-continued

```
Cys Lys Glu Val Val Ser Thr Leu Asp Ala Val Gln Val Leu Ser
        115                 120                 125
Gly Val Ser Gln Leu Leu Pro Lys Ser Arg Glu Asn Tyr Leu Asn Arg
    130                 135                 140
Cys Met Asp Gln Glu Arg Leu Arg Arg Glu Ser Thr Ser Gln Lys Glu
145                 150                 155                 160
Met Asp Lys Ala Glu Thr Lys Thr Lys Lys Ala Ala Glu Ser Leu Arg
                165                 170                 175
Arg Ser Val Glu Lys Tyr Asn Ser Arg Ala Asp Phe Glu Gln Lys
                180                 185                 190
Met Leu Asp Ser Ala Leu Arg Phe Gln Ala Met Glu Glu Thr His Leu
                195                 200                 205
Arg His Met Lys Ala Leu Leu Gly Ser Tyr Ala His Ser Val Glu Asp
    210                 215                 220
Thr His Val Gln Ile Gly Gln Val His Glu Glu Phe Lys Gln Asn Ile
225                 230                 235                 240
Glu Asn Val Ser Val Glu Met Leu Leu Arg Lys Phe Ala Glu Ser Lys
                245                 250                 255
Gly Thr Gly Arg Glu Lys Pro Gly Pro Leu Asp Phe Glu Ala Tyr Ser
                260                 265                 270
Ala Ala Ala Leu Gln Glu Ala Met Lys Arg Leu Arg Gly Ala Lys Ala
    275                 280                 285
Phe Arg Leu Pro Gly Leu Ser Arg Arg Glu Arg Glu Pro Glu Pro Pro
    290                 295                 300
Ala Ala Val Asp Phe Leu Glu Pro Asp Ser Gly Thr Cys Pro Glu Val
305                 310                 315                 320
Asp Glu Glu Gly Phe Thr Val Arg Pro Asp Val Thr Gln Asn Ser Thr
                325                 330                 335
Ala Glu Pro Ser Arg Phe Ser Ser Asp Ser Asp Phe Asp Asp Glu
                340                 345                 350
Glu Pro Arg Lys Phe Tyr Val His Ile Lys Pro Ala Pro Ala Arg Ala
    355                 360                 365
Pro Ala Cys Ser Pro Glu Ala Ala Ala Gln Leu Arg Ala Thr Ala
    370                 375                 380
Gly Ser Leu Ile Leu Pro Pro Gly Pro Gly Gly Thr Met Lys Arg His
385                 390                 395                 400
Ser Ser Arg Asp Ala Ala Gly Lys Pro Gln Arg Pro Arg Ser Ala Pro
                405                 410                 415
Arg Thr Ser Ser Cys Ala Glu Arg Leu Gln Ser Glu Glu Gln Val Ser
                420                 425                 430
Lys Asn Leu Phe Gly Pro Pro Leu Glu Ser Ala Phe Asp His Glu Asp
                435                 440                 445
Phe Thr Gly Ser Ser Ser Leu Gly Phe Thr Ser Ser Pro Ser Pro Phe
    450                 455                 460
Ser Ser Ser Ser Pro Glu Asn Val Glu Asp Ser Gly Leu Asp Ser Pro
465                 470                 475                 480
Ser His Ala Ala Pro Gly Pro Ser Pro Asp Ser Trp Val Pro Arg Pro
                485                 490                 495
Gly Thr Pro Gln Ser Pro Ser Cys Arg Ala Pro Pro Glu Ala
                500                 505                 510
Arg Gly Ile Arg Ala Pro Pro Leu Pro Asp Ser Pro Gln Pro Leu Ala
    515                 520                 525
Ser Ser Pro Gly Pro Trp Gly Leu Glu Ala Leu Ala Gly Gly Asp Leu
```

```
            530                 535                 540
Met Pro Ala Pro Ala Asp Pro Thr Ala Arg Glu Gly Leu Ala Ala Pro
545                 550                 555                 560

Pro Arg Arg Leu Arg Ser Arg Lys Val Ser Cys Pro Leu Thr Arg Ser
                565                 570                 575

Asn Gly Asp Leu Ser Arg Ser Leu Ser Pro Ser Pro Leu Gly Ser Ser
                580                 585                 590

Ala Ala Ser Thr Ala Leu Glu Arg Pro Ser Phe Leu Ser Gln Thr Gly
                595                 600                 605

His Gly Val Ser Arg Gly Pro Ser Pro Val Val Leu Gly Ser Gln Asp
                610                 615                 620

Ala Leu Pro Ile Ala Thr Ala Phe Thr Glu Tyr Val His Ala Tyr Phe
625                 630                 635                 640

Arg Gly His Ser Pro Ser Cys Leu Ala Arg Val Thr Gly Glu Leu Thr
                645                 650                 655

Met Thr Phe Pro Ala Gly Ile Val Arg Val Phe Ser Gly Thr Pro Pro
                660                 665                 670

Pro Pro Val Leu Ser Phe Arg Leu Val His Thr Thr Ala Ile Glu His
                675                 680                 685

Phe Gln Pro Asn Ala Asp Leu Leu Phe Ser Asp Pro Ser Gln Ser Asp
690                 695                 700

Pro Glu Thr Lys Asp Phe Trp Leu Asn Met Ala Ala Leu Thr Glu Ala
705                 710                 715                 720

Leu Gln Arg Gln Ala Glu Gln Asn Pro Thr Ala Ser Tyr Tyr Asn Val
                725                 730                 735

Val Leu Leu Arg Tyr Gln Phe Ser Arg Pro Gly Pro Gln Ser Val Pro
                740                 745                 750

Leu Gln Leu Ser Ala His Trp Gln Cys Gly Ala Thr Leu Thr Gln Val
                755                 760                 765

Ser Val Glu Tyr Gly Tyr Arg Pro Gly Ala Thr Ala Val Pro Thr Pro
                770                 775                 780

Leu Thr Asn Val Gln Ile Leu Leu Pro Val Gly Glu Pro Val Thr Asn
785                 790                 795                 800

Val Arg Leu Gln Pro Ala Ala Thr Trp Asn Leu Glu Glu Lys Arg Leu
                805                 810                 815

Thr Trp Arg Leu Pro Asp Val Ser Glu Ala Gly Ser Gly Arg Leu
                820                 825                 830

Ser Ala Ser Trp Glu Pro Leu Ser Gly Pro Ser Thr Pro Ser Pro Val
                835                 840                 845

Ala Ala Gln Phe Thr Ser Glu Gly Thr Thr Leu Ser Gly Val Asp Leu
850                 855                 860

Glu Leu Val Gly Ser Gly Tyr Arg Met Ser Leu Val Lys Arg Arg Phe
865                 870                 875                 880

Ala Thr Gly Met Tyr Leu Val Ser Cys
                885

<210> SEQ ID NO 6
<211> LENGTH: 887
<212> TYPE: PRT
<213> ORGANISM: Artificial
<220> FEATURE:
<223> OTHER INFORMATION: Fcho1 delta563-564

<400> SEQUENCE: 6

Met Ser Tyr Phe Gly Glu His Phe Trp Gly Glu Lys Asn His Gly Phe
```

```
              1               5                   10                  15
            Glu Val Leu Tyr His Ser Val Lys Gln Gly Pro Ile Ser Thr Lys Glu
                            20                  25                  30

Leu Ala Asp Phe Ile Arg Glu Arg Ala Thr Ile Glu Glu Thr Tyr Ser
                            35                  40                  45

Lys Ala Met Ala Lys Leu Ser Lys Leu Ala Ser Asn Gly Thr Pro Met
                            50                  55                  60

Gly Thr Phe Ala Pro Leu Trp Glu Val Phe Arg Val Ser Ser Asp Lys
             65                 70                  75                  80

Leu Ala Leu Cys His Leu Glu Leu Thr Arg Lys Leu Gln Asp Leu Ile
                            85                  90                  95

Lys Asp Val Leu Arg Tyr Gly Glu Glu Gln Leu Lys Thr His Lys Lys
                            100                 105                 110

Cys Lys Glu Glu Val Val Ser Thr Leu Asp Ala Val Gln Val Leu Ser
                            115                 120                 125

Gly Val Ser Gln Leu Leu Pro Lys Ser Arg Glu Asn Tyr Leu Asn Arg
                            130                 135                 140

Cys Met Asp Gln Glu Arg Leu Arg Arg Glu Ser Thr Ser Gln Lys Glu
            145                 150                 155                 160

Met Asp Lys Ala Glu Thr Lys Thr Lys Lys Ala Ala Glu Ser Leu Arg
                            165                 170                 175

Arg Ser Val Glu Lys Tyr Asn Ser Ala Arg Ala Asp Phe Glu Gln Lys
                            180                 185                 190

Met Leu Asp Ser Ala Leu Arg Phe Gln Ala Met Glu Glu Thr His Leu
                            195                 200                 205

Arg His Met Lys Ala Leu Leu Gly Ser Tyr Ala His Ser Val Glu Asp
                            210                 215                 220

Thr His Val Gln Ile Gly Gln Val His Glu Phe Lys Gln Asn Ile
            225                 230                 235                 240

Glu Asn Val Ser Val Glu Met Leu Leu Arg Lys Phe Ala Glu Ser Lys
                            245                 250                 255

Gly Thr Gly Arg Glu Lys Pro Gly Pro Leu Asp Phe Glu Ala Tyr Ser
                            260                 265                 270

Ala Ala Ala Leu Gln Glu Ala Met Lys Arg Leu Arg Gly Ala Lys Ala
                            275                 280                 285

Phe Arg Leu Pro Gly Leu Ser Arg Arg Glu Arg Glu Pro Glu Pro Pro
                            290                 295                 300

Ala Ala Val Asp Phe Leu Glu Pro Asp Ser Gly Thr Cys Pro Glu Val
            305                 310                 315                 320

Asp Glu Glu Gly Phe Thr Val Arg Pro Asp Val Thr Gln Asn Ser Thr
                            325                 330                 335

Ala Glu Pro Ser Arg Phe Ser Ser Asp Ser Asp Phe Asp Asp Glu
                            340                 345                 350

Glu Pro Arg Lys Phe Tyr Val His Ile Lys Pro Ala Pro Ala Arg Ala
                            355                 360                 365

Pro Ala Cys Ser Pro Glu Ala Ala Ala Gln Leu Arg Ala Thr Ala
                            370                 375                 380

Gly Ser Leu Ile Leu Pro Pro Gly Pro Gly Thr Met Lys Arg His
            385                 390                 395                 400

Ser Ser Arg Asp Ala Ala Gly Lys Pro Gln Arg Pro Arg Ser Ala Pro
                            405                 410                 415

Arg Thr Ser Ser Cys Ala Glu Arg Leu Gln Ser Glu Glu Gln Val Ser
                            420                 425                 430
```

-continued

```
Lys Asn Leu Phe Gly Pro Pro Leu Glu Ser Ala Phe Asp His Glu Asp
        435                 440                 445
Phe Thr Gly Ser Ser Ser Leu Gly Phe Thr Ser Ser Pro Ser Pro Phe
450                 455                 460
Ser Ser Ser Ser Pro Glu Asn Val Glu Asp Ser Gly Leu Asp Ser Pro
465                 470                 475                 480
Ser His Ala Ala Pro Gly Pro Ser Pro Asp Ser Trp Val Pro Arg Pro
                485                 490                 495
Gly Thr Pro Gln Ser Pro Pro Ser Cys Arg Ala Pro Pro Glu Ala
            500                 505                 510
Arg Gly Ile Arg Ala Pro Pro Leu Pro Asp Ser Pro Gln Pro Leu Ala
        515                 520                 525
Ser Ser Pro Gly Pro Trp Gly Leu Glu Ala Leu Ala Gly Gly Asp Leu
530                 535                 540
Met Pro Ala Pro Ala Asp Pro Thr Ala Arg Glu Gly Leu Ala Ala Pro
545                 550                 555                 560
Pro Arg Arg Ser Arg Lys Val Ser Cys Pro Leu Thr Arg Ser Asn Gly
                565                 570                 575
Asp Leu Ser Arg Ser Leu Ser Pro Ser Pro Leu Gly Ser Ser Ala Ala
            580                 585                 590
Ser Thr Ala Leu Glu Arg Pro Ser Phe Leu Ser Gln Thr Gly His Gly
        595                 600                 605
Val Ser Arg Gly Pro Ser Pro Val Val Leu Gly Ser Gln Asp Ala Leu
610                 615                 620
Pro Ile Ala Thr Ala Phe Thr Glu Tyr Val His Ala Tyr Phe Arg Gly
625                 630                 635                 640
His Ser Pro Ser Cys Leu Ala Arg Val Thr Gly Glu Leu Thr Met Thr
                645                 650                 655
Phe Pro Ala Gly Ile Val Arg Val Phe Ser Gly Thr Pro Pro Pro
            660                 665                 670
Val Leu Ser Phe Arg Leu Val His Thr Thr Ala Ile Glu His Phe Gln
        675                 680                 685
Pro Asn Ala Asp Leu Leu Phe Ser Asp Pro Ser Gln Ser Asp Pro Glu
690                 695                 700
Thr Lys Asp Phe Trp Leu Asn Met Ala Ala Leu Thr Glu Ala Leu Gln
705                 710                 715                 720
Arg Gln Ala Glu Gln Asn Pro Thr Ala Ser Tyr Tyr Asn Val Val Leu
                725                 730                 735
Leu Arg Tyr Gln Phe Ser Arg Pro Gly Pro Gln Ser Val Pro Leu Gln
            740                 745                 750
Leu Ser Ala His Trp Gln Cys Gly Ala Thr Leu Thr Gln Val Ser Val
        755                 760                 765
Glu Tyr Gly Tyr Arg Pro Gly Ala Thr Ala Val Pro Thr Pro Leu Thr
770                 775                 780
Asn Val Gln Ile Leu Leu Pro Val Gly Glu Pro Val Thr Asn Val Arg
785                 790                 795                 800
Leu Gln Pro Ala Ala Thr Trp Asn Leu Glu Glu Lys Arg Leu Thr Trp
                805                 810                 815
Arg Leu Pro Asp Val Ser Glu Ala Gly Gly Ser Gly Arg Leu Ser Ala
            820                 825                 830
Ser Trp Glu Pro Leu Ser Gly Pro Ser Thr Pro Ser Pro Val Ala Ala
        835                 840                 845
```

```
Gln Phe Thr Ser Glu Gly Thr Thr Leu Ser Gly Val Asp Leu Glu Leu
            850                 855                 860

Val Gly Ser Gly Tyr Arg Met Ser Leu Val Lys Arg Arg Phe Ala Thr
865                 870                 875                 880

Gly Met Tyr Leu Val Ser Cys
                885

<210> SEQ ID NO 7
<211> LENGTH: 19
<212> TYPE: DNA
<213> ORGANISM: Artificial
<220> FEATURE:
<223> OTHER INFORMATION: RNA oligonucleotides

<400> SEQUENCE: 7
agaccuacuc gaaggcgau                                                    19

<210> SEQ ID NO 8
<211> LENGTH: 19
<212> TYPE: DNA
<213> ORGANISM: Artificial
<220> FEATURE:
<223> OTHER INFORMATION: RNA oligonucleotides

<400> SEQUENCE: 8
ucaaggacgu ucuccgcua                                                    19

<210> SEQ ID NO 9
<211> LENGTH: 19
<212> TYPE: DNA
<213> ORGANISM: Artificial
<220> FEATURE:
<223> OTHER INFORMATION: RNA oligonucleotides

<400> SEQUENCE: 9
acguggugcu gcugcgaua                                                    19

<210> SEQ ID NO 10
<211> LENGTH: 19
<212> TYPE: DNA
<213> ORGANISM: Artificial
<220> FEATURE:
<223> OTHER INFORMATION: RNA oligonucleotides

<400> SEQUENCE: 10
ucucagugga guacggcua                                                    19

<210> SEQ ID NO 11
<211> LENGTH: 6
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 11

Arg Xaa Arg Xaa Xaa Ser
1               5

<210> SEQ ID NO 12
<211> LENGTH: 6
```

```
<212> TYPE: PRT
<213> ORGANISM: Mus musculus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 12

Arg Xaa Arg Xaa Xaa Ser
1               5

<210> SEQ ID NO 13
<211> LENGTH: 6
<212> TYPE: PRT
<213> ORGANISM: Homo sapiens

<400> SEQUENCE: 13

Arg Ser Arg Lys Val Ser
1               5

<210> SEQ ID NO 14
<211> LENGTH: 10
<212> TYPE: PRT
<213> ORGANISM: Artificial
<220> FEATURE:
<223> OTHER INFORMATION: FCHo1 fragment

<400> SEQUENCE: 14

Arg Arg Leu Arg Ser Arg Lys Val Ser Cys
1               5                   10

<210> SEQ ID NO 15
<211> LENGTH: 12
<212> TYPE: PRT
<213> ORGANISM: Artificial
<220> FEATURE:
<223> OTHER INFORMATION: FCHo1 fragment

<400> SEQUENCE: 15

Pro Pro Arg Arg Leu Arg Ser Arg Lys Val Ser Cys
1               5                   10

<210> SEQ ID NO 16
<211> LENGTH: 8
<212> TYPE: PRT
<213> ORGANISM: Artificial
<220> FEATURE:
<223> OTHER INFORMATION: FCho1 fragment

<400> SEQUENCE: 16

Pro Pro Arg Arg Leu Arg Ser Arg
1               5

<210> SEQ ID NO 17
<211> LENGTH: 6
<212> TYPE: PRT
<213> ORGANISM: Artificial
<220> FEATURE:
<223> OTHER INFORMATION: Akt binding motif

<400> SEQUENCE: 17

Arg Leu Arg Arg Glu Ser
1               5
```

```
<210> SEQ ID NO 18
<211> LENGTH: 6
<212> TYPE: PRT
<213> ORGANISM: Artificial
<220> FEATURE:
<223> OTHER INFORMATION: RSRKVS

<400> SEQUENCE: 18

Arg Ser Arg Lys Val Ser
1               5

<210> SEQ ID NO 19
<211> LENGTH: 25
<212> TYPE: PRT
<213> ORGANISM: Homo sapiens

<400> SEQUENCE: 19

Arg Glu Gly Leu Ala Ala Pro Pro Arg Arg Leu Arg Ser Arg Lys Val
1               5                   10                  15

Ser Cys Pro Leu Thr Arg Ser Asn Gly
            20                  25

<210> SEQ ID NO 20
<211> LENGTH: 25
<212> TYPE: PRT
<213> ORGANISM: Mus musculus

<400> SEQUENCE: 20

Arg Glu Gly Leu Ala Ala Thr Leu Arg Arg Pro Arg Ser Arg Lys Val
1               5                   10                  15

Ser Cys Pro Leu Thr Thr Ser Asn Gly
            20                  25

<210> SEQ ID NO 21
<211> LENGTH: 2623
<212> TYPE: DNA
<213> ORGANISM: Mus musculus

<400> SEQUENCE: 21
atgtcctatt ttggggaaca tttttggggc gacaaaaacc atggctttga ggtcctctac      60
cattgtgtga agcagggtcc tgtggccacc aaggagctgg ctgacttcat tagggaaagg     120
gccaacatcg aggagacata ctcgaaggcc atggccaaac tctccaagct agccagcaac     180 gggacccca tggggacctt tgccccgctc tgggaggtct ccgtgtgtc ctcggacaaa      240 ctggcactgt gccacctgga gcttactcgg aagctgcacg atctccttaa ggatgtgctg     300
cgctacggcg aggagcagct caagacccac aagaagtgta aggaggaagt tctaggcact     360
gtggatgcag tgcagatgtt gtcaggcgtc gggcagctcc tgccaaagtc tgcgcgagaa     420
ttacttgagc cgctgtatgg acctggagag actgcgtaga gaacaccca gccagaagga     480 gatggacaag gcagaaacca aaagcaagaa ggctgccgac agcctgcggc gctctgtgga     540
taaatacaac tcagcccgag ccgactttga gatcaagatg cttgattcag ccctgcgttt     600
tcaggccatg gaggaggcac atctgcagca catgaaggcc ttgctgggct cctatgcgca     660
ctctgtggag gacaccccatg tgcaaattgg gcaggtgcat gaggaattta gcagaatgt     720 ggaaaatgtg acgtggaca tgctcctcag gaaatttgca gagagcaagg gcaccgggcg     780
cgagaagcct gggcctctgg acttcgatgc atacagctca gctgccctgc aggaagcaat     840
gaaacgtctc cgtggagcca aggctttccg ccttccagga ttgagccgtc gggagccacg     900
```

```
tgcatctgtt gatttcctgg agtctgactc aggggtgcct ccagaggtag atgacgaagg    960
cttcactgtg cgccccgata tatctcagaa caatggggct gagccccccac gcttctcctc  1020
tagtgactct gattttgacg atgaggagcc tagaaagttc tatgttcaca tcaagcccgc   1080
ccccacccgc gccgtggcct gcagctctga ggctgcagct gcccagctca gggccacggc   1140
tggcagcctc atcctccctc caggcccagg gggcaccatg aaacgtcatt catcacggga   1200
cacttctggg aagccacaga gacctcgttc ggccccacgc actggcagtt gcgcagagaa   1260
gccccctggcc tcggaggagc cactgtccaa gagcctcttt gggccgccgc tggagtccgc  1320
cttcgaccac gatgacttca caggctccag cagcctgggc ttcacatcca gcccgtctcc   1380
tttctcatcc tcatctccgg agaatgtgga ggactcgggc ctggattctc cgtcacatgc   1440
tgcccctggt ccgtcacctg agtcctgggt ccccccggcca ggcacccccgc agagcccacc  1500
cacctgcagg gcacagcacc ctgagcccag gggcctaatg ccccgtgcac cctcaccagg   1560
tccctggggg cctgagggag gtgcagattc actgacgccg gctgacccca ccagggaggg   1620
cctagctgcc acactgagaa gaccacggtc caggaaagtg tcctgcccac tcaccaggag   1680
caatggggac ctgtgccggt cgctcagccc atccccactg ggatcctctg cccccaccat   1740
ccccccccgat cggcctagct tctccaccca gatgggacat ggcatctccc gtggcccag   1800
cccagtggtc ctgggatctc aggacaccct gcccgtggcc acagccttca ctgagtatgt   1860
ccatgcctat ttccgtggcc acagcccag ttgcctggct cgagtcaccg gggagttaac    1920
catgaccttc cctgcgggca ttgtgcgtgt gttcagtggc accccaccac cacctgtcct   1980
cagcttccgg ctggtgaaca cggccccctgt agaacactttc cagcccaacg ctgacctgat  2040
cttcagtgac cctcccagca gtgacccgga gaccaaagac ttctggctga atatggcggc   2100
gctgacggag gccctacagc accaggctga gcagaaccc accgcctcct actacaacct    2160
ggtgctattg cggtaccagt tctcccgccc tggacctgag tcagtgccccc tgcaaatgag   2220
cgccactgg cagtgcgggc ccacactcac gcgggtctcg gtggagtaca gctaccgtgc    2280
gggcgccact gctgtgtcca cgccactcac taatgtccag atcctcctgc ccgtggggga   2340
gccggtgacc agtgtgcggc tgcagcctgc ggccacctgg aacacagagg aaaagaggtt   2400
cacgtggaag cttccagatg tgtgtgaggc aggggggctca ggccacctgt cagccagctg   2460
gcagccgcag tcggggccca gcactcccag cccccgtggcc gcacaattca ccagtgaggg   2520
cgccacgctg tctggcctgg acctggagct gctaggtggt ggctaccgca tgtccctggt   2580
gaagcggaga ttcgctacag ggatgtacct tgtcagctgc tga                      2623
```

<210> SEQ ID NO 22  
<211> LENGTH: 42  
<212> TYPE: DNA  
<213> ORGANISM: Artificial  
<220> FEATURE:  
<223> OTHER INFORMATION: shmFCHo1_238

<400> SEQUENCE: 22

```
aaactggcac tgtgccacct ctcggtggca cagtgccagt tt                         42
```

<210> SEQ ID NO 23  
<211> LENGTH: 42  
<212> TYPE: DNA  
<213> ORGANISM: Artificial  
<220> FEATURE:  
<223> OTHER INFORMATION: ShmFCHo1_458

<400> SEQUENCE: 23
gagagaacac cagccagaat ctcttctggc tggtgttctc tc				42

<210> SEQ ID NO 24
<211> LENGTH: 42
<212> TYPE: DNA
<213> ORGANISM: Artificial
<220> FEATURE:
<223> OTHER INFORMATION: shmFCHo1_599

<400> SEQUENCE: 24
ttcaggccat ggaggaggct ctcgcctcct ccatggcctg aa				42

<210> SEQ ID NO 25
<211> LENGTH: 42
<212> TYPE: DNA
<213> ORGANISM: Artificial
<220> FEATURE:
<223> OTHER INFORMATION: ShmFCho1_1090

<400> SEQUENCE: 25
gccgtggcct gcagctctgt ctccagagct gcaggccacg gc				42

<210> SEQ ID NO 26
<211> LENGTH: 15
<212> TYPE: PRT
<213> ORGANISM: Homo sapiens

<400> SEQUENCE: 26

Val Thr Gly Glu Leu Thr Met Thr Phe Pro Ala Gly Ile Val Arg
1               5                   10                  15

<210> SEQ ID NO 27
<211> LENGTH: 29
<212> TYPE: PRT
<213> ORGANISM: Homo sapiens

<400> SEQUENCE: 27

Val Thr Gly Glu Leu Thr Met Thr Phe Pro Ala Gly Ile Val Arg Val
1               5                   10                  15

Phe Ser Gly Thr Pro Pro Pro Val Leu Ser Phe Arg
            20                  25

<210> SEQ ID NO 28
<211> LENGTH: 24
<212> TYPE: PRT
<213> ORGANISM: Homo sapiens

<400> SEQUENCE: 28

Gly His Ser Pro Ser Cys Leu Ala Arg Val Thr Gly Glu Leu Thr Met
1               5                   10                  15

Thr Phe Pro Ala Gly Ile Val Arg
            20

<210> SEQ ID NO 29
<211> LENGTH: 7
<212> TYPE: PRT
<213> ORGANISM: Artificial
<220> FEATURE:
<223> OTHER INFORMATION: FCHo1 fragment

<400> SEQUENCE: 29

Pro Pro Arg Arg Leu Arg Ser
1               5

COMPOSITION FOR REGULATING CELL DIVISION COMPRISING FCHO1 MODULATOR, AND METHOD FOR REGULATING CELL DIVISION USING SAME

This application is a National Stage Application of PCT/KR2016/013304, filed on Nov. 17, 2016, which claims priority to Korean Patent Application No. 10-2016-0153654, filed on Nov. 17, 2016 and Korean Patent Application 10-2015-0161326, filed Nov. 17, 2015. The entirety of the aforementioned applications is incorporated herein by reference.

TECHNICAL FIELD

The present invention relates to a composition for regulating cell division by promoting or inhibiting the activity of FCHo1 and a method using the same.

BACKGROUND ART

Cell division is an essential process which is carried out to compensate for the growth of living things and natural loss of life, which is a critical process in the maintenance of life. Therefore, cell division is carried out through a very sophisticated and complicated process. When such cell division occurs, diseases such as cancer may occur.

Cancer is one of the major diseases that humankind needs to conquer, which has the characteristic of abnormally proliferating the cells that should be in a resting state due to defects in cell division, thereby destroying the surrounding cells. These cancers are known to occur as genetic mutations of various factors involved in the signal transduction pathway that regulates cell growth and differentiation.

When eukaryotic cells receive signals for cell growth from outside, they proliferate according to the cell cycle through the signal transduction pathway. Eukaryotic cells proliferate by periodically going through DNA synthesis phase (referred to as S phase), and the mitosis phase (referred to as the M phase). Between the S phase and the M phase, there are a G1 phase and a G2 phase, and thus the cells are divided through the G1-S-G2-M cycle in turn. After cell division is complete, the cells enter the G1 phase, which is the most active stage of intracellular metabolism, and most cells are present in the G1 phase for many hours. Cells in the G1 phase are diploid, i.e., 2N. DNA replication occurs in the S phase, and 2N becomes tetraploid, 4N. After the G2 phase, 4N is divided into 2N in the short M phase. They return to the G1 phase again. In normal cells, if there is a growth stimulus signal from the outside in the G1 phase, the cell enters the S phase, and then cell division occurs through the G2 phase to allow proliferation. When there is no external signal, the cell cycle is stopped, and the cell enters G0 phase (resting phase) which is stopped in the G1 phase.

The mitosis is frequently observed in cells that are actively dividing. The chromatins are condensed, and chromosomes are formed. At the same time, a spindle or a cleavage apparatus with a microtubule skeleton is formed. The mitosis is characterized in that the chromosomes are bisected to both ends on the spinous body and the fission is completed. The mitosis is divided into prophase, metaphase, and anaphase. In metaphase, the chromosomes to which the spindle is connected are arranged on the equatorial plane of the cell. In anaphase, the paired chromosomes are separated vertically and split into two, and they move to both ends by the spindle. In telophase, spindle disappears, the asteroid body becomes the midbody, the nuclear membrane and phosphorus appear, and two new daughter nuclei are formed.

On the other hand, cancer cells proliferate while the cells that should be in resting phase, regardless of the external signal, continue DNA synthesis and cell division according to the cell cycle. To determine the resting phase and the cell division cycle, the cell cycle factors of each phase should be present in the cell so that the cell cycle can be accurately performed, and there must be a receptor that receives an external signal. Therefore, if the functions of receptors and cell cycle factors that determine the boundary between the resting phase and the cell division cycle are distorted, the cells will grow abnormally and be transformed into cancer cells.

Therefore, it is a very interesting subject to regulate the cell division of cancer cells for the treatment of cancer cells. However, it is not yet known about the regulation of cancer cell division through regulation of midbody formation.

DISCLOSURE

Technical Problem

While the present inventors have conducted studies to develop a new therapeutic agent by regulating the cell division and further regulating the cell division of the cancer cell, they have found that FCHo1 protein is an essential factor involved in the formation of the midbody during cell division, and cell division can be effectively regulated by targeting this, thereby completing the present invention.

Therefore, the present invention relates to a composition for regulating cell division including an FCHo1 activity regulator and a method for regulating cell division ability using the same.

Technical Solution

The present invention provides a composition for regulating cell division including an FCHo1 (FCH domain only 1) activity regulator.

Further, the present invention provides a cell division regulator including an FCHo1 (FCH domain only 1) activity regulator.

Further, the present invention provides a media composition including an FCHo1 (FCH domain only 1) activity regulator.

Further, the present invention provides a method for providing information about cell division ability, including detecting FCHo1 (FCH domain only 1) in a cell.

Further, the present invention provides a method for regulating cell division ability of animals, including regulating FCHo1 (FCH domain only 1) activity.

Further, the present invention provides a method for regulating cell division ability, including regulating FCHo1 (FCH domain only 1) activity in vitro.

Further, the present invention provides a pharmaceutical composition for preventing or treating cancer, including an FCHo1 (FCH domain only 1) activity regulator.

Further, the present invention provides a therapeutic agent for cancer, including an FCHo1 (FCH domain only 1) activity regulator.

Further, the present invention provides a method for providing information on cancer diagnosis on an individual, including detecting an FCHo1 (FCH domain only 1) protein fragment.

Further, the present invention provides a composition for diagnosing cancer, including a detection agent of FCHo1 (FCH domain only 1) protein fragment.

Advantageous Effects

The FCHo1 activity regulator of the present invention targets FCHo1 which is an important factor in cell division to promote or inhibit its activity, thereby promoting cell division or inhibiting cell division so that it can be utilized effectively to treat cell division-related diseases.

DESCRIPTION OF DRAWINGS

FIG. 1 is a schematic view illustrating the structure of FCHo1 and its cleavage site.

FIG. 2 illustrates the result of confirming the site-specific cleavage of FCHo1 through the specific deletion form of FCHo1.

FIG. 3 illustrates the result of confirming the site-specific cleavage of FCHo1 through the specific deletion form of FCHo1 in which the asterisk indicates that the band has disappeared.

FIG. 4 illustrates the result of confirming the sub-cellular location of a cleaved FCHo1 protein fragment using an FCHo1 antibody.

FIG. 5 illustrates the result of confirming inhibition of FCHo1 cleavage by MG132 treatment in which the asterisk indicates that the band has disappeared.

FIG. 6 illustrates the result of predicting that matrix metallopeptidase 9 (MMP-9) cleaves FCHo1 at Arg 563 (R563) position.

FIG. 7 illustrates the result of immunoprecipitation for wild-type (wt) (SEQ ID NO: 5) or FCHo1 (Δ563-564 (SEQ ID NO: 6) or Δ531-589).

FIG. 8 illustrates PLA result of FCHo1 and MMP-9 (scale bar, 5 μm).

FIG. 9 illustrates the result of confirming the sites of FCHo1 and its fragments according to the cell division step (scale bar, 5 μm).

FIGS. 10a and 10b illustrate FESEM results of midbody in which a denotes a horizontal cutting plane, and b denotes a vertical cutting plane.

FIGS. 10c and 10d illustrate detection results of FCHo1 presence in the vehicle through immuno-gold labeling.

FIG. 10e illustrates the result of confirming the FCHo1 site through a super-resolution microscopy (SRM) (Three-dimensional SIM, 3D-SIM, direct stochastic optical reconstruction microscopy (dSTORM)) (scale bar, 1 μm).

FIG. 11 illustrates CLSM images for identifying the site of FCHo1 during cell division.

FIG. 12 illustrates an Akt binding motif in FCHo1.

FIG. 13 illustrates the results of confirming FCHo1 and Akt binding site.

FIG. 14 is a schematic view illustrating the Akt1 phosphorylation site of FCHo1 and its position in the midbody and ICB.

FIG. 15 illustrates the result of confirming the self-binding of FCHo1 through the co-immunoprecipitation method.

FIG. 16 illustrates the result of confirming cleavage of F-BAR fragments in the cell division step in which the asterisk indicates that the band has disappeared.

FIG. 17 illustrates the result of confirming the cellular position of F-BAR and CT fragments through immunofluorescence and PLA analysis.

FIG. 18 illustrates the result of confirming the inhibitory effect of FCHo1 cleavage in the S570A mutation structure.

FIG. 19 illustrates the result of confirming the binding of FCHo1 and 14-3-3ζ.

FIG. 20 illustrates the results of confirming the binding site of 14-3-3ζ through co-immunoprecipitation and PLA analysis.

FIG. 21 illustrates the result of confirming that the binding of FCHo1 and 14-3-3ζ is essential for the formation of the midbody.

FIG. 22 illustrates the result of confirming SIM images of midbody images of wild-type FCHo1 or FCHo1 Δ563-564 expression A549 cell.

FIG. 23 illustrates the results of (A) confirming the change of the cell cycle-related protein group in A549 cells overexpressing FCHo1 by the proteomic analysis and (B) confirming that the protein located in the midbody is regulated by overexpression of FCHo1.

FIG. 24 illustrates the result of quantifying the ratio of cells in anaphase (spindle) and telophase (midbody) through the CLSM image.

FIG. 25 illustrates the results of confirming lesions and the number of tumor cells in the FCHo1 wild type, its mutant treatment group in a lung cancer model mouse.

FIG. 26 illustrates four shRNA sequence designs acting on mouse FCHo1.

FIG. 27 illustrates the result of confirming changes in FCHo1 cleavage in normal tissues and 1,2,3-group lung cancer tissues of human samples.

FIG. 28 illustrates the result of confirming the binding affinity between the peptide derived from the FCHo1 amino acid sequence and Akt1.

FIG. 29 illustrates the result of confirming the intracellular uptake of the peptide derived from the FCHo1 amino acid sequence.

FIG. 30 illustrates the result of confirming the cell growth inhibitory effect of the peptide derived from the FCHo1 amino acid sequence.

BEST MODE

The present invention relates to a composition for regulating cell division, which includes an FCHo1 (FCH domain only 1) activity regulator.

FCHo1 of the present invention is a protein involved in midbody formation through site-specific cleavage during cell division. It plays an essential role in cell division, especially in the mitosis phase. The FCHo1 activity regulator targets this to regulate the cell division, thereby effectively treating various diseases related to the cell division, particularly cancers.

The FCHo1 is listed as Gene ID: 23149 in human FCHo1, which is a protein composed of FER/Cip4 homology Bin-Amphiphysin-Rvs (F-BAR) domain, a proline-rich domain (PRD), and mu-homology domain (MHD). It is a protein that plays a vital role in the formation of the midbody located at the center of the intracellular cellular bridge (ICB) at the end of the cytoplasmic division during the cell division.

The midbody has a knee-joint-like structure that connects two daughter cells at the end of the cell division, which is characterized by being regulated by FCHo1 according to the present invention.

The FCHo1 regulates the formation of the midbody through site-specific cleavage, and such cleavage sites can occur at positions between PRD and MHD domains and between F-BAR and PRD. The corresponding site may be cleaved by MMP-9.

The site-specific cleavage of FCHo1 occurs as the cell division progresses and its cleaved C-terminal fragment remains in the midbody, but the N-terminal fragment is located in the intracellular cellular bridge (ICB) at the end of cell division. Further, each segment is moved after cleavage.

Therefore, the present invention relates to a composition for regulating cell division in which the FCHo1 activity regulator is for regulating midbody formation.

In the present invention, the FCHo1 activity regulator refers to a substance capable of promoting or inhibiting FCHo1 activity. Here, the FCHo1 activity means 'activity in which FCHo1 forms midbody, and further cell division occurs normally.' Thus, an FCHo1 activity promoter refers to a substance capable of promoting cell division by promoting the role of FCHo1 in the cell division step. For example, the FCHo1 activity promoter is composed of a substance promoting the site-specific cleavage of FCHo1 (MMP-9), a substance promoting proper phosphorylation of FCHo1 (Akt1), and a substance promoting the binding of FCHo1 to 14-3-3ζ. It may include, without limitation, gene transcription and expression control substances known in the art such as an FCHo1 specific promoter capable of promoting FCHo1 specific transcription or expression. Further, an FCHo1 activity inhibitor refers to a substance that prevents FCHo1 from performing cell division normally by inhibiting or destroying its role in the cell division stage. For example, the FCHo1 activity inhibitor may be a substance that inhibits the site-specific cleavage of FCHo1, an FCHo1 phosphorylation inhibitor, a binding inhibitor between 14-3-3ζ and FCHo1, and an FCHo1 mutant or an FCHo1 deletion sequence.

In particular, the mutant or deletion sequence of FCHo1 is mutation or deletion occurred in the sequence cleaved by matrix metallopeptidase 9 (MMP-9) in FCHo1 sequence, which may be a sequence in which normal site-specific cleavage of FCHo1 is prevented from inhibiting cell division. It is mutation or deletion occurred in the phosphorylation site due to Akt1 of the FCHo1 sequence, which may be a sequence in which Akt1 is prevented from normally binding to FCHo1, thereby blocking normal cleavage of FCHo1. It may be a sequence in which mutation or deletion occurs in the binding site with 14-3-3ζ of the FCHo1 sequence to interfere with the binding, thereby interfering with the midbody formation.

An exemplary FCHo1 inhibitor may include various inhibitors prepared by genetic engineering techniques inhibiting their protein expression and their gene expression. For example, it may include one or more selected from the group consisting of antisense nucleotide complementarily binding to mRNA of FCHo1 gene, short hairpin RNA (shRNA), small interfering RNA (siRNA), and a ribozyme. It may include one or more selected from the group consisting of a compound specifically binding to an FCHo1 protein, a peptide, a peptide mimetic, a substrate analog, an aptamer, and an antibody.

Thus, the present invention relates to a composition for regulating cell division in which the FCHo1 activity inhibitor inhibits the site-specific cleavage of FCHo1. Further, the present invention relates to a composition for regulating cell division in which the FCHo1 activity inhibitor is an FCHo1 phosphorylation inhibitor.

Further, the present invention relates to a composition for regulating cell division in which the FCHo1 activity inhibitor is a binding inhibitor between 14-3-3ζ and FCHo1; in which the FCHo1 activity inhibitor is an FCHo1 mutant or an FCHo1 deletion sequence; in which the FCHo1 mutant or the FCHo1 deletion sequence is mutated in a sequence cleaved by matrix metallopeptidase 9 (MMP-9) in FCHo1 sequences; in which the FCHo1 mutant or the FCHo1 deletion sequence is a mutation or deletion occurred at the phosphorylation site by Akt1 in the FCHo1 sequence; or the FCHo1 mutant or the FCHo1 deletion sequence is a sequence in which a mutation or deletion occurs at a binding site with 14-3-3ζ of the FCHo1 sequence.

In the present invention, the cell in which the cell division is regulated is not limited in its kind. However, it may be a cell having a disease associated with abnormal cell division, particularly preferably cancer cells, for particularly useful purposes.

Further, the present invention relates to a cell division regulator including the FCHo1 activity regulator.

The cell division regulator regulates cell division in an individual to be used to treat diseases and disorders related to the cell division.

The disease related to cell division may be cell proliferative disorder such as cancer with abnormal cell division, various intractable diseases caused by non-cancerous abnormal proliferation-cell division, or various intractable diseases due to abnormally low cell division. The cell proliferative disorder includes, but are not limited to, tumors, malignant tumors, blood vessel proliferative disorders, autoimmune disorders and fibrotic disorders.

This abnormal proliferation may mean that cell division occurs at an inappropriately high level beyond the normal cell proliferation level.

Further, the present invention relates to a media composition including an FCHo1 activity regulator.

The term "media" used herein refers to a culture medium capable of supporting the growth and survival of cells under in vitro culture conditions, which includes all conventional culture media used in the art suitable for culture. Further, medium and culture conditions may be selected depending on the type of cells. The medium used for the culture is preferably a cell culture minimum medium (CCMM), which generally includes a carbon source, a nitrogen source, and a trace element component. For example, the cell culture minimum medium may include, but be not necessarily limited to, Dulbecco's Modified Eagle's Medium (DMEM), Minimal Essential Medium (MEM), Basal Medium Eagle (BME), RPMI1640, F-10, F-12, Glasgow's Minimal Essential Medium (GMEM), Iscove's Modified Dulbecco's Medium, and the like.

Further, the present invention relates to a method for providing information about cell division ability, which includes detecting FCHo1 (FCH domain only 1) in a cell According to the method of the present invention, FCHo1 may be detected in a cell, and its activity may be detected, thereby effectively providing information on whether the midbody is normally formed and cell division ability as to whether the cell division is normally performed. If abnormal mutations occur in FCHo1, and thus site-specific cleavage of FCHo1 is not normally performed, the midbody may be abnormally formed in the cell division step so that the cell division ability may be reduced.

Therefore, the detection may include detection of one or more selected from the group consisting of FCHo1 cleavage, FCHo1 phosphorylation, FCHo1 migration to the midbody, and the like.

In particular, FCHo1 plays an essential role in the formation of midbody appearing during cell division so that information on the cell division ability may be information on the ability of the midbody formation.

Further, the present invention provides a method for regulating cell division ability of animals, which includes regulating FCHo1 (FCH domain only 1) activity.

Since the FCHo1 of the present invention is essential for the formation of the midbodies during the cell division, FCHo1 activity is regulated to regulate cell division ability effectively.

For example, the regulation means that the FCHo1 activity is inhibited to induce the inhibition of midbody formation, thereby regulating so that the normal cell division does not occur. The inhibition of FCHo1 activity may be carried out by FCHo1 activity inhibitor.

The animal cell may be an animal cell other than a human or an animal cell including a human. In particular, it may be a cell derived from an individual having a disease associated with cell division, for example, cancers.

Further, the present invention provides a method for regulating cell division ability, which includes regulating FCHo1 (FCH domain only 1) activity in vitro.

According to the present invention, FCHo1 activity is regulated in vitro in cells isolated from an individual to regulate the cell division ability, which can be usefully used for mechanism studies or diseases related to cell division.

Further, the present invention provides a pharmaceutical composition for preventing or treating cancer, which includes an FCHo1 (FCH domain only 1) activity regulator.

The EST analysis was performed on FCHo1 transcripts in various cancer tissues. The results revealed that FCHo1 is highly transcribed in cancer tissues, particularly in B-lymphoblast, bone marrow, muscle, and ovarian cancer tissues, and is highly transcribed in bone, eye, lung, pancreas, placenta, skin, colon, stomach, and testis. Thus, FCHo1 of the present invention, which functions in mitosis and is present in cells more rapidly divided, can be a target for the treatment of various cancers. Further, FCHo1 activity is regulated to prevent or treat cancer caused by various abnormal cell proliferations.

Cancer may include, without limitation, cancers caused by abnormal cell division or mitosis. However, the cancer may be one or more selected from the group consisting of lung cancer, stomach cancer, colon cancer, liver cancer, bone cancer, pancreatic cancer, skin cancer, head or neck cancer, melanoma in skin or eyeball, uterine cancer, ovarian cancer, rectal cancer, anal cancer, breast cancer, fallopian tube carcinoma, endometrial carcinoma, cervical cancer, vaginal carcinoma, vulvar carcinoma, Hodgkin's disease, esophageal cancer, small bowel cancer, endocrine cancer, thyroid cancer, parathyroid cancer, adrenal cancer, soft tissue sarcoma, urethral cancer, penile cancer, prostate cancer, chronic or acute leukemia, lymphocytic lymphoma, bladder cancer, renal or ureteral cancer, renal cell carcinoma, renal pelvic carcinoma, CNS tumors, primary CNS lymphomas, spinal cord tumors and solid cancer such as brainstem glioma and pituitary adenoma. Further, it may include one or more selected from the group consisting of B-lymphoblast, bone marrow cancer, muscle cancer, ovarian cancer, bone cancer, eye cancer, lung cancer, pancreatic cancer, placental cancer, skin cancer, colon cancer, gastric, cancer and testicular cancer.

The FCHo1 activity regulator regulates FCHo1 activity to regulate abnormal cell division of cancer cells appropriately. For example, the abnormal FCHo1 cleavage is induced, or FCHo1 mutant or deletion sequence is introduced to inhibit FCHo1 activity, thereby inhibiting cancer cell division.

Therefore, the present invention relates to a therapeutic agent for cancer, which includes the FCHo1 (FCH domain only 1) activity regulator.

The mutant or deletion sequence of FCHo1 is mutation or deletion occurred in the sequence cleaved by matrix metallopeptidase 9 (MMP-9) in the FCHo1 sequence, which may be a sequence in which normal site-specific cleavage of FCHo1 is prevented from inhibiting cell division. It is mutation or deletion occurred in the phosphorylation site due to Akt1 of the FCHo1 sequence, which may be a sequence in which Akt1 is prevented from normally binding to FCHo1, thereby blocking normal cleavage of FCHo1. It may be a sequence in which mutation or deletion occurs in the binding site with 14-3-3ζ of the FCHo1 sequence to interfere with the binding, thereby interfering with the midbody formation. More specifically, it may be, based on the human FCHo1 sequence, a mutation or deletion sequence of the S570 site, a mutation or deletion sequence of the S155 region, a mutation or deletion sequence of R563-564 region of FCHo1 and a mutation or deletion sequence of 407-421aa of FCHo1.

The introduction of the mutant or deletion sequence of FCHo1 can be carried out without limitation by methods known in the art. A mutant or deletion sequence of FCHo1 is introduced into a suitable vector such as a lentiviral vector as an embodiment of the present invention, and thus it can be introduced into an individual with cancer.

The pharmaceutical compositions of the present invention may be prepared in a variety of parenteral or oral administration forms according to known methods. Representative examples of formulations for parenteral administration may include aerosol formulations and injectable formulations.

Solid preparations for oral administration include tablets, pills, powders, granules, capsules, and the like, which may be prepared by mixing at least one excipient such as starch, calcium carbonate, sucrose or lactose, gelatin with the active ingredients. Lubricants such as magnesium stearate and talc may also be used in addition to simple excipients.

Liquid preparations for oral administration include suspensions, solutions, emulsions, syrups, and the like. In addition to simple diluents such as water and liquid paraffin, various excipients such as wetting agents, sweeteners, perfumes, preservatives, and the like may be included.

Preparations for parenteral administration include sterile aqueous solutions, non-aqueous solutions, suspensions, emulsions, freeze-dried preparations, and suppositories. Examples of the non-aqueous solution and suspension may include propylene glycol, polyethylene glycol, vegetable oils such as olive oil, injectable esters such as ethyl oleate, and the like. As a substrate for the suppository formulation, WITEPSOL, Macrogol, twin 61, cacao butter, laurin butter, or glycerogelatin may be used.

In particular, a preferred formulation of the pharmaceutical composition of the present invention may be an inhalation dosage formulation (aerosol formulation) formulated to be delivered to the target site by aerosol delivery.

Drug delivery via inhalation is one of the non-invasive methods in which drugs pass through the airways and then the mucosa of the lungs to be directly delivered to the lung cells. In particular, it may be advantageously used to deliver nucleic acid for extensive treatment of lung diseases via aerosol delivery. This is because the anatomy and location of the lung allow an immediate, non-invasive approach, and the nucleic acid delivery system can be topically applied to the lung without affecting other organs. Therefore, when the mutant or deletion sequence of FCHo1 of the present invention is combined with a proper transporter to be delivered to a lesion site including the lung and the like in an aerosol manner, the preventive or therapeutic effect of the disease can be expected.

In the present invention, the pharmaceutical composition may preferably include other ingredients, and the like which may synergize the main effect to the extent that does not impair the intended primary effect of the present invention.

Further, the pharmaceutical composition of the present invention may further include pharmaceutically acceptable carriers, excipients, and diluents in addition to the active ingredients for administration as described above.

Examples of carriers, excipients and diluents include one or more selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oils.

The effective dosage of the pharmaceutical composition of the present invention may vary depending on the patient's age, gender and weight, but may be administered in the range of 0.0001 mg/kg to 50 mg/kg, preferably 0.001 mg/kg to 20 mg/kg.

For the prevention or treatment of cancer, the composition of the present invention may be used alone or in combination with methods of surgery, chemotherapy, radiotherapy, hormone therapy, drug therapy and a process in which biological response modifiers are used.

Further, the present invention provides a method for providing information on cancer diagnosis on an individual, which includes detecting an FCHo1 (FCH domain only 1) protein fragment.

The individual is preferably a mammal including a human. The method for providing information on cancer diagnosis includes detecting an FCHo1 protein fragment and comparing the fragment with that of the normal object. When the result indicates that the FCHo1 protein fragment is reduced compared with that of the normal object, it is diagnosed as an individual having cancer.

Further, the present invention provides a composition for diagnosing cancer, which includes a detection agent of FCHo1 (FCH domain only 1) protein fragment.

The FCHo1 protein fragment refers to a fragment of the FCho1 protein cleaved by site-specific cleavage of FCHo1 in the mitotic phase of the cell division. Preferably, the individual is a human, and thus it refers to the FCHo1 protein fragment prepared by site-specific cleavage at the Arg563 site.

The FCHo1 protein fragment detection agent refers to a preparation capable of measuring the protein level by a method in which a specific antibody is used to allow contacting a protein fragment with a biological sample derived from an individual, thereby forming an antigen-antibody complex. For analyzing these, specific analysis methods include, but are not limited to, Western blotting, ELISA, radioimmunoassay, radial immunodiffusion, Ouchterlony immunodiffusion, rocket immunoelectrophoresis, tissue immunostaining, immunoprecipitation assay, complement fixation assay, FACS, protein chip, and the like. ELISA includes various ELISA such as a direct sandwich ELISA using another labeled antibody recognizing antigens in a complex of antibody and antigen attached to a solid support and an indirect sandwich ELISA using a labeled secondary antibody recognizing the other antibodies after reacting with other antibodies recognizing antigens in a complex of antibody and antigen attached to a solid support.

Hereinafter, the present invention will be described in detail with Examples and preparation examples. However, the following Examples and preparation examples are merely illustrative of the present invention, and the contents of the present invention are not limited by the following Examples and preparation examples.

MODES OF THE INVENTION

Cell Culture and Transfection

A549 cells used in the experiments were cultured in DMEM/high glucose medium supplemented with 10% FBS and penicillin/streptomycin at 37° C. and 5% $CO_2$. The cells were transfected using Neon® transfection system.

Plasmid, siRNA and Compound

All plasmid constructs were cloned by In-fusion® HD cloning kit (Clontech® Laboratories). Human FCHo1 cDNA clone, pCMV6-N-3×DDK vector and pCMV6-C-3×DDK vector were purchased from Origene and used. The generated clones are as follows: FCHo1-N-3×DDK, FCHo1-N-3×DDK mutation (Δ273-294, S295A), FCHo1-C-3×DDK, FCHo1-C-3×DDK mutation (Δ150-155, Δ480-561, Δ531-561, Δ562-569, Δ562-570, Δ571-579, Δ580-589, Δ563-564, Δ531-589, 407-421), FCHo1-C-3×DDK double mutation (Δ150-155 and Δ562-570), partial FCHo1-C-3×DDK (562-889, 582-889, 1-268), partial FCHo1 (1-268)-C-3×DDK mutation (Δ150-155) and partial FCHo1 (562-889)-C-3×DDK mutation (R562N, R563N, L564G, S566A, R567N, K568N, V569G, S570A, C571N). FCHo1 siRNA resistant clone: siRNA resistant FCHo1-C-3×DDK and siRNA resistant FCHo1-C-3×HA. The following pairs of RNA oligonucleotides were synthesized to the target human FCHo1: AGACCUACUCGAAGGCGAU (dtdt) (SEQ ID NO: 7), UCAAGGACGUUCUCCGCUA (dtdt) (SEQ ID NO: 8), ACGUGGUGCUGCUGCGAUA (dtdt) (SEQ ID NO: 9), UCUCAGUGGAGUACGGCUA (dtdt) (SEQ ID NO: 10). Nocodazole was purchased and used from Sigma-Aldrich, and MG132 was purchased and used from MP Biomedicals.

Immunofluorescence

A549 cells were placed in 8-well chamber cover glasses or high-precision cover glasses and were fixed with 3% paraformaldehyde for 10 minutes at room temperature, permeabilized with 0.5% TRITON® X-100 (Sigma-Aldrich) for 5 min, blocked for 30 minutes. Then, the cells were incubated with primary or secondary antibodies in blocking solution (PBS with 0.1% saponin and 3% BSA). Alexa Fluor 647 conjugated anti-rabbit secondary antibody and an oxygen scavenging system (0.5 mg/ml glucose oxidase, 40 μg/ml catalase, 10% glucose, pH 7.4) were used for stochastic optical reconstruction microscopy (dSTORM) imaging. Before imaging, 30 mM mercaptoethylamine (MES; Sigma) was added to obtain a final thiol concentration of 10-200 mM. All dSTORM and SIM images were obtained from Carl Zeiss ELYRA PS.1 (super-resolution microscopy), and all CLSM images were obtained from the Carl Zeiss LSM710 (confocal laser scanning microscope).

Antibody

FCHo1 (NBP2-16458; 584-804aa) was purchased and used from Novus Biologicals; FCHo1 (SAB2100803; 468-517aa) and FLAG-HRP (A8592) were purchased and used from Sigma-Aldrich; FCHo1 (HPA041653; 285-364aa) was purchased and used from Atlas Antibodies; Aktl (LF-MAO245) was purchased and used from Abfrontier; Gamma-Tubulin (ab11316), Calmodulin 1 (ab106681), RACGAP1 (ab2270), FCHo1 (ab102994; 92-242aa) and HA-HRP (ab 1190) were purchased and used from Abcam;

MKLP-1 (sc-867) and 14-3-3° C. (sc-1019) were purchased and used from Santa Cruz; Phospho-Akt substrate (RXRXXS (SEQ ID: 11)/T-p) (#10001) was purchased and used from Cell signaling; 14-3-35 (H00007534-M04) and MMP-9 (H00004318-M03) were purchased and used from Abnova; and Alexa Fluor 488, 555, or 647 labeled anti-mouse or rabbit antibodies were purchased and used from Life Technologies.

Immunoprecipitation and Immunoblotting

The cells were dissolved in IP dissolution buffer for 30 min at 4° C. After centrifugation at 17,000×g for 30 minutes, the concentration of the protein was measured, and the same amount of lysate was used for immunoprecipitation. The immunoprecipitation was carried out overnight at 4° C. using anti-FLAG $M^2$ affinity gel (Sigma-Aldrich). The precipitate was washed three times with washing solution, and the precipitated proteins were separated using SDS-PAGE. Western blotting was carried out using anti-rabbit antibodies conjugated with specific antibodies and secondary anti-mouse IgG Veriblot or horseradish peroxidase. The results were visualized using a chemiluminescence detector (Atto Ez-Capture MG).

Gelatin Zymography

For gelatin zymography, immunoprecipitation (IP) was carried out in 10% SDS-PAGE containing 0.1% gelatin. IP samples were carried out on SDS-PAGE gels and washed with 2.5% TRITON X-100. Then, they were incubated for 3 days with collagenase buffer containing 50 mM TrisCl (pH 7.6), 0.2 M NaCl, 5 mM $CaCl_2$) and 0.2% Brij-35. The gel was stained with Coomassie Brilliant Blue and desalted.

In Situ Proximity Ligation Assay (PLA)

PLA was performed on SIM image protein-protein interactions using a high-resolution fluorescence microscope. Proximity ligation was performed using a Duolink detection kit according to the manufacturer's manual. All PLA images were collected with Carl Zeiss's ELYRA PS.1.

FIB-FESEM

A549 cells were fixed in pH 7.2-7.4, 0.1 M cacodylate buffer with 2.5% glutaraldehyde for 1 hour, washed with distilled water, fixed in 0.1 M cacodylate buffer with 0.5% osmium tetraoxide (NaOH), and further washed with distilled water. En_bloc staining was then performed with 0.1-0.5% uranyl acetic acid in 50% ethanol overnight, followed by dehydration and infiltration. Images were obtained with FEI's Helios 650 (FIB-FESEM).

Pre-Embedding Immuno-Gold TEM (Gold Enhancement)

A549 cells were fixed in a mixture of 4% paraformaldehyde and 0.05% glutaraldehyde in 0.15 M Hepes, post-fixed in 4% paraformaldehyde in 0.15 M Hepes and washed. Samples were blocked, incubated with the FCHo1 antibody (584-804aa), washed, incubated with secondary antibodies with nanogold (Nanoprobes, Yaphank, NY, USA) and washed again. After fixation with 1% glutaraldehyde, the results were washed with 50 mM glycine and then with 1% BSA. Other samples were fixed with a 1:1 mixture of 2% osmium tetraoxide and 3% potassium ferrocyanide, dehydrated and then infiltrated. Images were obtained using JEOL's JEM1010 (TEM at 80 kV acceleration voltage).

Preparation of Sample for Proteomic Analysis

Proteins were extracted from the cell lines using RIPA buffer. The protein concentration was determined using the bicinchoninic acid assay kit. The protein lysates were digested using filtered-aided sample preparation (FASP). 200 µg protein was denatured in SDT buffer (4% SDS, 0.1 M DTT and 0.1 M Tris/HCl, pH 7.6) and then reduced for 45 minutes at 37° C. For protein alkylation, 50 mM iodoacetamide (IAA) was added for 30 minutes at room temperature and under a dark condition. In order to remove reagents and the like, the samples were centrifuged using UA buffer (8 M urea, 0.1 M Tris-HCl and pH 8.5). Then, the UA buffer was replaced with TEAB buffer (100 mM, pH 8.5). Sequencing-grade trypsin (Promega, USA) was added (trypsin:protein=1:50 [w/w] in 100 mM TEAB), and then the result was incubated for 12 hours at 37° C. TMT reagent was used to label the degraded samples in accordance with the manufacturer's manual. At this step, triplicate samples of the two conditions were separately labeled with each channel as follows: control sets #1, #2, and #3 were labeled with 126, 128, and 130 channels; FCHo1-overexpressing sets #1, #2, and #3 were labeled with 127, 129, and 131 channels. Equal amounts of the labeled peptides were pooled and then fractionated using a 3100 OFFGEL fractionator (Agilent Technologies, USA). After fractionation, each fraction was desalted using a C18 spin column.

LC-MS/MS Analysis

The peptide samples were analyzed by nano-LC-MS/MS using Q-Exactive (Thermo Fisher Scientific, Germany). The peptide samples were analyzed by nano-LC-MS/MS. The peptide samples were loaded on the trap column (PepMap, 2 cm×75 µm, 3 µm particle size, Thermo Scientific) and separated using an EASY-Spray column (PepMap, 50 cm×75 µm, 2 µm particle size, Thermo Scientific) at 0.3 µl/min using solvent A (0.1% formic acid in water) and solvent B (0.1% formic acid in acetonitrile). A separate gradient program was then set as follows: linear 5-40% B for 160 min, linear 40-80% B for 2 min, isocratic 80% for 10 min, linear 80-5% B for 2 min and isocratic 5% B for 15 min. The column temperature was maintained at 60° C. The precursor ion scans were acquired in a profile mode with an AGC target value of $3\times10^6$ and a mass resolution of 70 K at m/z 200. The top 10 precursor ions in the MS scan were selected using an orbitrap analyzer. The product ions were generated by higher energy collisional dissociation (HCD) fragmentation with normalized collision energy (NCE).

TMT Data Analysis

The raw data were searched against the human database (Uniprot/Swissprot, release-Apr_2014, 89601 entries) using the SEQUEST® search engine on Proteome Discoverer 1.4 (Thermo Scientific). The searches were performed using the following parameters: tolerance set to 10 ppm for precursor ions and 0.8 Da for fragment ions; maximum allowable number of missed cleavages was 1; TMT modification of lysine and free amine in the amino terminus and carbamidomethylation of cysteine were set as fixed modifications; and methionine oxidation was set as a variable modification. To validate the identification of the peptides and proteins, Peptide Prophet and Protein Prophet algorithms were applied using Scaffold Q+ (version 4.3.3, Proteome Software Inc., USA). Thresholds of peptide probability were used as >95%, and thresholds of protein probability were used as >99%. The protein identification was considered "correct" if it was assigned by at least two unique peptides. The peak intensities of the TMT reporter ions were extracted from the tandem mass spectra using Scaffold Q+. Subsequently, the relative ratio of abundance of the proteins and both p-values (sample p-value, ratio p-value) were calculated with between the two groups (126/127, 128/129, 130/131) using Isobar (R software package). The proteins were selected in the FCHo1-overexpressing cells as having both p-values (sample p-value and ratio p-value)<0.05. Gene ontology (GO) analysis was performed with the significant proteins using the DAVID Bioinformatics resource.

Example 1: Identification of FCHo1 Cleavage Site

It is known that at the end of cytokinesis, FCHo1 is present in the midbody located at the center of the intracellular cellular bridge (ICB), and FCHo1 is known to be associated with early working proteins at the surface of clathrin assembled as a nucleic acid coat nucleator. As illustrated in FIG. 1, FCHo1 consists of an FER/Cip4 homology Bin-Amphiphysin-Rvs (F-BAR) domain, a proline-rich domain (PRD), and a mu-homology domain (MHD). F-BAR domain forms a crescent-shaped antiparallel dimer structure which binds to PtdIns(4,5)P$_2$-enriched membranes. The underline at the bottom of the sequence illustrated in FIG. 1 refers to the sequence corresponding to the site recognized by the various FCHo1 antibodies, and the vertically labeled region in the sequence represents the potential FCHo1 cleavage site.

In order to confirm whether site-specific cleavage of FCHo1 regulates the formation of the midbody, the cleavage site of FCHo1 was first identified. Immunoblot analysis was performed with an anti-FLAG antibody from cells that were transfected with full-length wild-type, Δ273-294, or S295A in which FCHo1 N-terminal constructs were fused with 3×FLAG in A549 cells. Representative immunoblot analysis was performed with an anti-FLAG antibody after transfection of full-length wild-type or site-specific deletion of FCHo1 proteins (Δ480-561, Δ531-561, Δ562-569, Δ562-570, or Δ571-579) with C-terminally fused 3×FLAG tag in A549 cells. The immunoblot analysis results are illustrated in FIGS. 2 and 3.

As illustrated in FIG. 2, it was apparently confirmed that the band disappeared at Δ273-294. Further, as illustrated in FIG. 3, it was confirmed that the band disappears at Δ562-569 and Δ562-570. Thus, it was confirmed that FCHo1 was cleaved at positions between the PRD and MHD domains and at positions between F-BAR and PRD. In other words, the regions of FCHo1 cleaved by the predictive cleavage site are the F-BAR domain, the proline-rich domain (PRD), and the mu homology domain (MHD).

Example 2: Identification of FCHo1 Protein Fragment Specifically Located in Midbody To determine whether the cleaved FCHo1 protein fragments have different subcellular localizations, four antibodies targeting different sites of FCHo1 were employed (92-242aa, 285-364aa, 468-517aa or 584-804aa). A confocal laser scanning microscopy (CLSM) was used to obtain microscopy images of FCHo1. Mitosis-synchronized A549 cells were stained with four different FCHo1 antibodies and Hoechst 33342 (DNA stain). The results are illustrated in FIG. 4.

As illustrated in FIG. 4, α584-804 antibody stained the midbody such as a knee-joint-like structure connecting two daughter cells at the final stage of cell division, whereas the other FCHo1 antibodies (α92-242 and α468-517) stained the intracellular bridge (ICB). In other words, it was confirmed that FCHo1 was site-specific cleaved, and the fragments containing 584-804aa of the cleavage sites were specifically located in the midbody.

Example 3: Identification of Proteolytic Enzyme Cleaving FCHo1

To test the potential involvement of specific proteases to cleave FCHo1, the cells were treated with 1 μM MG132, a protease inhibitor for 16 hours. Immunoblotting of the A549 cell extract was performed in the presence or absence of the MG132 protease inhibitor, and the results are illustrated in FIG. 5.

As illustrated in FIG. 5, the cleaved FCHo1 protein completely disappeared in the MG132-treated sample, indicating that FCHo1 cleavage could be affected by a specific protease. Then, the FCHo1 amino acid sequence was analyzed using PROSPER. Impressively, the analysis predicted that matrix metallopeptidase 9 (MMP-9) was the protease responsible for FCHo1 cleavage at Arg563 (R563) (See FIG. 6).

Based on these results, to determine whether MMP-9 binds and cleaves FCHo1 at R563, immunoprecipitation of the wild-type (wt) or 563-564 or 531-589aa deleted (Δ) FCHo1 (Δ563-564 or Δ531-589) proteins was performed in mitotic phase using FLAG antibodies. Thereafter, zymography was performed on MMP-9, and the results are illustrated in FIG. 7. Further, FCHo1 (584-804) and MMP-9 proximity ligation assay (PLA) were performed in midbody formation, and the results are illustrated in FIG. 8.

As illustrated in FIG. 7, zymography revealed that the activity of MMP-9 is suppressed in FCHo1 deletion mutations Δ563-564 and Δ531-589 compared with the wild-type. Further, as illustrated in FIG. 8, it was confirmed that FCHo1 and MMP-9 clearly interacted with each other at the midbody. The results indicate that the R563 site of FCHo1 is cleaved by an MMP-9 protease.

Example 4: Examination of Localization of FCHo1 and its Fragments According to Cell Division To examine the localization of the cleaved FCHo1 fragments during midbody formation, two FCHo1 antibodies (α468-517 or α584-804) were used to monitor the presence of the N-terminal (NT) and C-terminal (CT) fragments of FCHo1 cleaved at R563. The location of the FCHo1 fragment was confirmed at the end of the mitosis and telophase, after the midbody formation, for the purpose of identifying the location of the midbody formation. Structured-illumination (SIM) images were obtained by immunostaining at the telophase. To examine the migration and location of each fragment at anaphase and telophase, the ectopic Δ563-564 protein which is an siRNA-resistant FCHo1 construct was expressed, and the location of the FCHo1 fragment by α468-517 or α584-804 in ectopic FCHo1 was confirmed. These results are illustrated in FIG. 9.

As illustrated in FIG. 9, at the anaphase of mitosis, both α468-517 and α584-804 stained the central spindles, while at telophase, after the midbody formation, α584-804 stained the midbody, but α468-517 stained ICB. Interestingly, α468-517 stained ICB at anaphase of cells with normal FCHo1, but the α468-517 stained the midbody area at telophase in the ectopic Δ563-564-expressing cells. However, in the case of α584-804, it remained in the midbody without a change in the ectopic FCHo1 Δ563-564 as normal FCHo1. These results indicate that FCHo1 is located in the central spindle during the telophase. However, as the cell division progresses, R563 of FCHo1 is cleaved by MMP-9 during the midbody formation. Thus, the CT fragment remains at the midbody, while the NT fragment is located at the ICB.

Example 5: Confirmation of Midbody-Specific Location of FCHo1 and Location According to Progression of Cell Division To dissect the nanoscale structure of the midbody where FCHo1 is located, field emission scanning electron microscopy (FESEM) and TEM analysis were carried out. The results are illustrated in FIG. 10. In the TEM, FCHo1 antibody (α584-804) was used to detect the presence of FCHo1 in the vehicle via immuno-gold labeling. Further, super-resolution microscopy (SRM) using FCHo1 antibody (α584-804) or calmodulin 1 was performed to additionally confirm the position of FCHo1. A typical CLSM image during cell division is illustrated in FIG. 11. A549 cells were stained with FCHo1 antibody (α584-804), calmodulin antibody and Hoechst 33342 (DNA stain).

FIG. 10 illustrates that the midbody was darkly stained due to its electron-dense structure, and vehicles were abundant in the midbody and ICB (See a and b). Further, the α584-804 gold staining was frequently observed at the borders of the midbody (See c, Post-embedding) and stained the vehicle membrane (See d, Pre-embedding). Super-resolution microscopy (SRM) also showed that FCHo1 was gathered at the border of the midbody (See e).

As illustrated in FIG. 11, it was confirmed that FCHo1 detected by antibody α584-804 strongly appeared during the midbody formation and persisted in the midbody until cytoskeletal cleavage occurred in cell division.

Example 6: Confirmation of Akt1 Substrate Motif of FCHo1 and its Cleavage Characterization As illustrated in FIG. 12, there are two Akt1 binding motifs such as Ser155 (S155) and Ser570 (S570) in FCHo1, which are conserved with mouse FCHo1. To evaluate whether Akt1 binds at S570 in the RxRxxS (SEQ ID: 12) motif, co-immunoprecipitation of endogenous Akt1 was carried out using FLAG antibodies for anti-3×FLAG-fused partial FCHo1 construct (562-889 or 582-889) expression. Further, Akt1 binding site was identified using the co-immunoprecipitation for the 150-155 deletion mutation (F-BAR Δ150-155) of FCHo1. The results are illustrated in FIG. 13.

As illustrated in FIG. 13, 562-889 bound to Akt1, but 582-889 (RxRxxS deleted construct) did not bind to Akt1, indicating that the 565-570aa region (RSRKVS, SEQ ID: 13) of FCHo1 corresponds to the motif of Akt1 substrate (See a). Further, the result of co-immunoprecipitation using F-BAR Δ150-155 indicates that Akt1 binds to the F-BAR domain (1-268aa), and Akt1 binding is weakly observed in its deletion F-BAR Δ150-155. Thus, although the Akt1 binding motif of the F-BAR domain is removed, Akt1 interacted with F-BAR Δ150-155 to some extent, indicating that the F-BAR domain has a homodimer (See b). The Akt1 phosphorylation site of FCHo1 and its location in the midbody and ICB are illustrated in FIG. 14.

To examine whether FCHo1 is self-binding, C-terminal HA-fused or FLAG-fused FCHo1 (FCHo1-HA or FCHo1-FLAG) and FCHo1 siRNA were co-transfected, and anti-FLAG antibody against FCHo1-FLAG was used to perform co-IP of FCHo1-HA. The results are illustrated in FIG. 15.

As illustrated in FIG. 15, interestingly, FCHo1-FLAG bound to the full-length FCHo1-HA, while FCHo1-FLAG did not bind to the CT-fragment (564-889aa) of FCHo1-1HA. Therefore, these results indicate that NT fragments associated with the F-BAR domain are essential for dimerization or multimerization of FCHo1.

Co-immunoprecipitation of Akt1 with anti-FLAG antibody was performed. A549 cells were transfected with full length-FCHo1, cleaved 75 kDa CT fragment and cleaved 38 kDa CT fragment, and the results of the analysis are illustrated in FIG. 16.

As illustrated in FIG. 16, the 38 kDa-CT fragment was abundantly observed during the interphase but was weakly detected during the cell division (mitosis), and the newly cleaved 75 kDa CT fragment was more clearly detected during the cell division. A red star in the figure indicates that no 75 kDa C-terminal fragment (F-BAR cleavage) was detected.

These results indicate that cleavage of R563 during cell division occurs less during the interphase and a 75 kDa CT-fragment band is observed. If FCHo1 is cleaved in Glu269 (E269), the CT fragment including 3×FLAG (3 kDa) is approximately 74 kDa. The 74 kDa was confirmed to be similar to the 75 kDa band of 269-889-3×FLAG without the F-BAR domain, indicating that the F-BAR domain was cleaved during mitosis.

Example 7: Location and Interaction of FCHo1 and Akt1 in Midbody

Immunofluorescence and PLA assays confirmed whether the F-BAR domain binds to Akt1 at the ICB and plasma membrane and FCHo1 and Akt1 interact in the midbody. SIM images of FCHo1 and Akt1 were observed in the midbody which midbody was magnified. Interaction of FCHo1 and Akt1 in the midbody was confirmed by PLA, and Calmodulin 1 was used as an ICB marker. The results are illustrated in FIG. 17.

As illustrated in FIG. 17, α-192-242 stained ICB while α-584-804 stained the midbody. In other words, although Akt1 and F-BAR are co-located, it was confirmed that the CT-fragment binds to Akt1 in the midbody. These results indicate that the F-BAR domain and the CT-fragment have different subcellular localizations (ICB or midbody) and that Akt1 may also bind to each Akt1-binding motif of the two fragments (F-BAR domain or the CT-fragment) in different locations (ICB or midbody). Therefore, it was assumed that the F-BAR domain (1-268) was cleaved from FCHo1 (1-889) and F-BAR (1-268) was translocated in ICB during mitosis. The F-BAR domain appears to be associated with Akt1 in Pleckstrin homology (PM) during mitosis, and its function is thought to be associated with the intracellular cleavage pathway.

Example 8. Cleavage Inhibition of FCHo1 by FCHo1 S570A Mutation

R563 cleavage site of FCHo1 was found, which was located adjacent to the Akt1 binding motif (565-570aa) of FCHo1. An FCHo1 S570A mutant construct was generated to abolish FCHo1 phosphorylation at S570. The SIM image of the S570A mutation construct was identified by staining the midbody with the FCHo1 antibody (α468-517). A549 cells were observed for the wild-type FCHo1 or FCHo1 mutation (S570A). The results are illustrated in FIG. 18.

As illustrated in FIG. 18, S570A mutation changed the staining of FCHo1 antibody from ICB to the midbody. NT fragment of FCHo1 cleaved at R563 was detected. This change was similar to the results from Example 3, where the FCHo1 Δ563-564 mutant inhibited FCHo1 cleavage at R563. Therefore, it suggests that FCHo1 cleavage at R563 is dependent on Akt1.

Example 9: Confirmation of Inter-Binding of FCHo1 and 14-3-3ζ and its Influence on Midbody Formation The 14-3-3ζ is a heterotetramer composed of MKLP1 kinesin-6 and CYK4 RhoGAP, which are known as homologous molecules of human MKLP1 and RACGAP1, respectively. The central spindle functions for the formation and maintenance of the midbody. The 14-3-3ζ is a dispersed protein of the midbody-derived RACGAP1/MKLP1 complex.

Co-immunoprecipitation was performed using an anti-FLAG antibody to identify whether the interaction partner of FCHo1 was 14-3-3ζ. A549 cells were transfected with full-length FCHo1, cleaved FCHo1 and 14-3-3ζ. Transfected cells were identified in mitosis or in the interphase. The results are illustrated in FIG. 19.

As illustrated in FIG. 19, the binding of 14-3-3ζ to FCHo1 was confirmed, and this binding increased at the mitosis rather than at the interphase. Further, PLA analysis demonstrated that 14-3-3ζ binds to FCHo1 in the midbody.

To verify the predictive binding site of 14-3-3ζ for FCHo1, 407-421aa, FCHo1 Δ407-421 construct was generated, and co-immunoprecipitation of 14-3-3ζ and Akt1 was performed using anti-FLAG antibody. Transfected cells were observed at the time of mitosis. Further, PLA analysis confirmed the interaction of FCHo1 (584-804) with 14-3-3ζ in the midbody. The results are illustrated in FIG. 20.

As illustrated in FIG. 20, Δ407-421 inhibited the binding of 14-3-3ζ to FCHo1 (See a). Further, PLA test results indicated that 14-3-3ζ bound to FCHo1 (584-804) in the midbody (See b).

Further, as illustrated in FIG. 21, Δ407-421 strongly abolished midbody formation in mitosis. This indicated that 14-3-3ζ bound to 407-421aa of FCHo1 and that this binding was essential for the midbody formation.

SIM images of midbody of wild-type FCHo1 or FCHo1 Δ563-564 expression A549 cells were additionally confirmed. Cells were stained with FCHo1 (α584-804), 14-3-3ζ, MKLP1 and RACGAP1 antibodies. The midbody region was enlarged and observed, and the results are illustrated in FIG. 22.

As illustrated in FIG. 22, it was confirmed that α14-3-3ζ stained Δ563-564 more strongly than FCHo1 in the midbody. Further, Δ563-564 sequestered the stable clustering of MKLP1/RACGAP1 at the midbody. These results indicate that the damage of FCHo1 cleavage at R563 causes an accumulation of the 14-3-3ζ at the midbody, which may lead to blocking aberrant clustering of the MKLP1/RACGAP1 complex.

Example 10: Change of Midbody-Associated Protein Expression by Overexpression of FCHo1

Proteins that were up and down regulated clearly by FCHo1 overexpression were analyzed by mass spectrometry. The changes in cell cycle-related protein groups in A549 cells overexpressing FCHo1 were confirmed by proteomic analysis. The results are illustrated in FIG. 23.

As illustrated in FIG. 23, FCHo1 overexpression promoted the down-regulation of the cell cycle-related protein group, while proteins of the mitochondrial electron transport-related protein group were upregulated (See a). All proteins in the midbody were modulated by FCHo1 overexpression (See b). It suggests that FCHo1 is a key factor that regulates midbody-related proteins.

In the analysis using the synchronization method, the cells were stained with MKLP1 antibody for the central spindle or midbody type analyses. The rates of cells in anaphase (central spindle) and telophase (midbody) were quantified via CLSM images: FCHo1 siRNA (n=318), wt FCHo1 (n=702), FCHo1 Δ563-564 (n=756) and FCHo1 Δ531-589 (n=1952). The results are illustrated in FIG. 24.

As illustrated in FIG. 24, Δ563-564 protein inhibited the midbody formation compared with wild-type FCHo1 protein.

FCHo1 was newly identified as a novel midbody regulator based on the results as described above. FCHo1 was cleaved site-specifically by a protease, and fragments of site-specific cleavage were differentially translocated into the midbody or ICB. Akt1, known as a kinase, phosphorylates FCHo1 at S155 and S570. The phosphorylation at S570 was important to cleave FCHo1, and the phosphorylation at S570 was carried out by R563 cleavage-dependent Akt1. The R563-564 deletion mutation inhibited midbody formation and unstably formed RACGAP1 and MKLP1, known as components of the central spindle. FCHo1 cleavage induced blocking the accumulation of 14-3-3ζ in the midbody. This maintains the stability of the MKLP1/RACGAP1 complex, through which FCHo1 regulates midbody formation. The 407-421aa deletion mutation abrogated midbody formation, suggesting that 14-3-3ζ binding to FCHo1 is required for midbody formation. The midbody protein FCHo1 is essential for midbody function and can effectively regulate midbody formation through regulation of the site-specific cleavage of FCHo1.

Example 11: Confirmation of Anticancer Effect by FCHo1 Regulation 11.1 Confirmation of Tumor Size and Volume Reduction by FCHo1 Deletion and Mutation Type Lentiviral vectors were prepared for the full-length, mutation type and deletion type of FCHo1 and transferred to lung cancer model mouse in a non-invasive aerosol method. Then their anticancer effects were confirmed. Example 8 confirmed that the sites involved in FCHo1 cleavage in human cells were FCHo1$^{S570A}$ and FCHo1$^{del563-564}$. Therefore, corresponding positions were confirmed in mouse FCHo1. It was confirmed that S570A corresponded to S554A and del563-564 corresponded to del544-545. The lentiviral vectors were prepared on the basis of these results, and the 9-week-old K-ras female mice were inhaled and exposed thereto total 8 times for 4 weeks. Then, the anticancer effects thereof were compared. The results are illustrated in FIG. 25.

As illustrated in FIG. 25, the total number of tumors significantly decreased in FCHo1$^{S554A}$ and FCHo1$^{del544-545}$ (n=7). Further, results of observation of tumor volume revealed that FCHo1$^{S554A}$ showed a significant decrease in volume compared with FCHo1$^{wt}$ and FCHo1$^{del544-545}$ also showed a decrease in volume. Based on these results, it was found that FCHo1 mutation and deletion form may inhibit tumors by inhibition of midbody formation.

11.2 Pathologic Analysis by FCHo1 Cleavage Inhibition

H&E slides were prepared to confirm whether adenoma and hyperplasia were reduced. The results are shown in Table 1. The shFCHo1 was used for FCHo1 cleavage inhibition. The sequence thereof is represented in SEQ ID NOs: 1 to 4 based on FIG. 26. The shmFCHo1 of SEQ ID NO: 2 had the most significant FCHo1 inhibitory effect. Therefore, this was used to perform this experiment.

TABLE 1

|  | No. of Mouse | No. of Adeno-carcinoma | No. of Adenoma | No. of hyperplasia foci |
| --- | --- | --- | --- | --- |
| Con | 5 | 0.20 ± 0.45 | 2.00 ± 0.71 | 1.80 ± 0.45 |
| V.Con | 5 | — | 0.80 ± 1.10 | 1.60 ± 1.14 |
| WT | 5 | — | 2.00 ± 1.22 | 0.80 ± 0.84* |
| S554A | 5 | — | 0.60 ± 0.55**,% | 1.00 ± 1.00 |
| Δ544-545 | 5 | 0.20 ± 0.45 | 0.60 ± 0.55**,% | 0.40 ± 0.55** |

TABLE 1-continued

| | No. of Mouse | No. of Adeno-carcinoma | No. of Adenoma | No. of hyperplasia foci |
|---|---|---|---|---|
| shSCR | 5 | — | 1.40 ± 0.89 | 2.00 ± 1.22 |
| shFCHo1 | 5 | 0.20 ± 0.45 | 0.60 ± 0.55** | 0.60 ± 0.55**,# |

As described in Table 1, the deletion type and mutation group of FCHo1 showed significant inhibition of adenoma and hyperplasia compared with the control group. These indicated that the normal FCHo1 cleavage inhibition induced an abnormality in the cell division, thereby inhibiting differentiation and thus exhibiting anticancer effects.

11.3. Identification of FCHo1 Cleavage Reduction in Lung Cancer Tissue

Changes in FCHo1 cleavage were observed in normal tissues of human samples and in lung cancer tissues with stages 1, 2, and 3. The amount of FCHo1 expression was detected using an antibody that targets and detects 584-804aa including a portion of the MHD domain region of FCHo1. The results are illustrated in FIG. 27.

As illustrated in FIG. 27, it was confirmed that the FCHo1 fraction with 25 kDa or less was remarkably reduced or disappeared in lung cancer tissues compared with normal lung tissues. These fragments were analyzed with a mass spectrometer to obtain results including FCHo1 642-665aa. This was caused by cleavage of Arg563. This result reflected the fact that lung cancer tissues were in the mitosis. This result indicated that the FCHo1 fragment was invisible or small compared with normal individuals, suggesting that the FCHo1 fragment may be used as a marker for cancers.

Example 12: Development of Peptide Anticancer Therapeutic Agent Using FCHo1 Binding Site To confirm the binding affinity between Akt1 and Akt1 motif-containing FCHo1 amino acid sequence-derived peptides, biotin was conjugated to peptides to complete the synthetization. The peptides were reacted and attached to on the streptavidin-attached plate. After treating with the cell lysates, the binding affinity of the peptide and Akt1 was confirmed by the Akt1 antibody. The experiment process and its result of confirming in vitro binding affinity of Akt1 according to respective peptides derived from FCHo1 binding sites are illustrated in FIG. 28.

As illustrated in FIG. 28, Akt1 binding affinity significantly increased in peptides 562-571 of FCHo1 (RRLRSRKVSC, SEQ ID: 14) and 560-571 of FCHo1 (PPRRLRSRKVSC, SEQ ID: 15). They included Akt1 binding motifs. The purpose of developing peptide therapeutic agents is to develop antagonists competing with FCHo1 binding partners by short-chain peptides derived from FCHo1 binding sites for Akt1, MMP9, and 14-3-3. Therefore, they were expected to inhibit FCHo1 cleavage, inhibit phosphorylation or inhibit the binding of binding partners, which are expected to be used in the development of peptide anticancer therapeutic agents.

Example 13. Confirmation of Peptide Absorption into Cell

Biotin-conjugated peptides were treated to cells and fixed on the cells, followed by reaction with streptavidin-488 fluorescent dye, followed by observation with CLSM. The results are illustrated in FIG. 29.

FIG. 29 illustrated that the peptide 560-571 (PPRRLRSRKVSC, SEQ ID: 15) showed an increase in absorption into a cell in a concentration-dependent manner. The limitations of peptide therapeutic agents are that they may not be absorbed into cells well due to the nature of the peptide such as the charge or hydrophilicity, thereby requiring use of carriers or conjugation of myristic acid to the peptide. However, the 560-571 peptides have the advantage of overcoming the limitations of the peptide therapeutic agents because the peptide itself is well absorbed into the cells. These demonstrate that the peptide itself can permeate the cell membrane without requiring conjugation of a separate cell penetrating peptide (CPP) and carrier, indicating that it is valuable as an effective therapeutic agent.

Example 14: Identification of Cell Growth Rate Change by Peptide

Cell viability was measured using Xcelligence for in real time observation, and the peptides were treated in 10 μM. 560-567, 562-571, and 560-571 peptides showed inhibitory effects on the cell growth. The results are illustrated in FIG. 30.

As illustrated in FIG. 30, peptides 560-567, 562-571, and 560-571 showed inhibitory effects on cell growth. Particularly, the peptide 560-571 (PPRRLRSRKVSC, SEQ ID: 15) showed the excellent inhibitory effect on cell growth as they showed excellent binding affinity with Akt1 and excellent absorption into cells. Therefore, it was confirmed that the Akt1 binding motif and 14-3-3 binding site of FCHo1 were excellent target sites for the development of peptide anticancer agents and chemicals.

Preparation Example 1: Preparation of Medicines 1.1 Preparation of Powder
  FCHo1 activity regulator: 100 mg
  Lactose: 100 mg
  Talc: 10 mg
  The components are mixed and packed in an airtight bag to prepare powders.

1.2 Preparation of Tablet
  FCHo1 activity regulator: 100 mg
  Cornstarch: 100 mg
  Lactose: 100 mg
  Magnesium stearate: 2 mg
  The components are mixed and tableted according to a conventional tablet preparation to prepare tablets.

1.3 Preparation of Capsule
  FCHo1 activity regulator: 100 mg
  Cornstarch: 100 mg
  Lactose: 100 mg
  Magnesium stearate: 2 mg
  The components are mixed according to a conventional capsule preparation and filled in gelatin capsules to prepare capsules.

1.4 Preparation of Injection
  FCHo1 activity regulator: 100 mg
  Sterile distilled water for injection: suitable amount
  pH regulator: suitable amount
  Injection is prepared to include the components per 1 ampoule (2 ml) according to a conventional injection preparation.

1.5 Preparation of Liquid Agent
  FCHo1 activity regulator: 100 mg
  Sugar: 20 g
  Isomerized sugar: 20 g
  Lemon: suitable amount
  Purified water was added to adjust the total volume to 1.00 ml. The components are mixed according to a conventional liquid agent preparation, then filled in a brown bottle and sterilized to prepare liquid agents.

The invention claimed is:

1. A method for treating a cancer, the method comprising administering an FCHo 1 activity inhibitor to a human subject that has cancer,
   wherein the FCHo1 inhibitor is selected from the group consisting of:
   human FCHo1$^{S570A}$ consisting of SEQ ID NO: 5 with the single mutation S570A, and
   human FCho1 del563-564 consisting of SEQ ID NO: 6,
   wherein the FCHo1 inhibitor is delivered into target cells by a pharmaceutically acceptable delivery system.

2. The method of claim 1, wherein the cancer includes one or more selected from the group consisting of B-lymphoblast cancer, bone marrow cancer, muscle cancer, ovarian cancer, bone cancer, eye cancer, lung cancer, pancreatic cancer, placental cancer, skin cancer, colon cancer, gastric cancer and testicular cancer.

3. The method of claim 1,
   wherein the pharmaceutical acceptable delivery system is a lentiviral vector.

* * * * *